United States Patent [19]
Kvalnes et al.

[11] Patent Number: 6,068,834
[45] Date of Patent: *May 30, 2000

[54] SKIN LIGHTENING COMPOSITIONS

[75] Inventors: Kalla Lynn Kvalnes; Mitchell Anthony DeLong; Barton James Bradbury; Curtis Bobby Motley, all of West Chester; John David Carter, Cincinnati, all of Ohio

[73] Assignee: The Procter & Gamble Company, Cincinnati, Ohio

[*] Notice: This patent is subject to a terminal disclaimer.

[21] Appl. No.: 08/390,152

[22] Filed: Feb. 24, 1995

Related U.S. Application Data

[63] Continuation-in-part of application No. 08/206,573, Mar. 4, 1994, abandoned.

[51] Int. Cl.[7] .................................................... A61K 7/48
[52] U.S. Cl. ............................. 424/62; 424/59; 424/456; 424/464; 424/489; 514/938; 549/28; 549/66; 549/346; 549/416; 568/51; 568/592; 568/649; 568/650
[58] Field of Search ................................ 424/62, 59, 456, 424/464, 489; 514/938; 549/28, 66, 346, 416; 568/51, 592, 649, 650

[56] References Cited

U.S. PATENT DOCUMENTS

| | | | |
|---|---|---|---|
| 4,764,505 | 8/1988 | Fujinuma et al. | 514/35 |
| 5,310,730 | 5/1994 | Fujinuma et al. | 514/35 |
| 5,346,693 | 9/1994 | Pilleux et al. | 424/62 |

FOREIGN PATENT DOCUMENTS 63-8314  1/1988  Japan.

*Primary Examiner*—Jyothsan Venkat
*Attorney, Agent, or Firm*—Richard A. Hake; Loretta J. Henderson; David L. Suter

[57] ABSTRACT

This invention relates to compositions, compounds and methods for lightening skin, using active compounds having the structure:

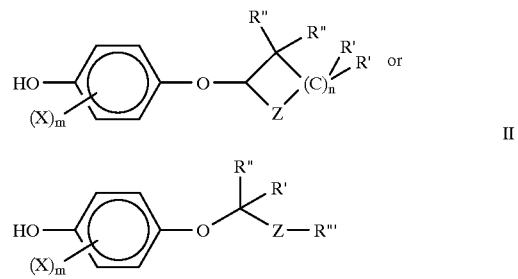

wherein:
(i) each X is, independently, selected from the group consisting of halo, alkyl, substituted alkyl, aryl, OR, OCOR, COR, CONRR COOR, CN, SR, SOR, $SO_2R$, $SO_3R$ and NRR, wherein X is other than hydroxy, amino and thio, if this X is attached ortho to the phenol hydroxy;
(ii) m is an integer from 0 to 4;
(iii) each R' and each R" is, independently, selected from the group consisting of hydrogen, halo, alkyl, substituted alkyl, aryl, OR, OCOR, OCRROR, COR, CR(OR)OR, CONRR, COOR, CRROR, CN, SR, and NRR; wherein halo, when it appears, is other than geminal to a hydroxy, $NH_2$, or SH;
(iv) R'" is alkyl or substituted alkyl; wherein when R'" is present, wherein when R'" is present and R' is also hydrogen, R" is other than hydrogen, hydroxy, halo, thio, cyano and amino;
(v) each R is, independently, selected from the group consisting of hydrogen, alkyl, substituted alkyl and aryl;
(vi) n is an integer from 1 to about 5, wherein at least one carbon in (C)n has other than alkyl or hydroxy as a substituent and (C)n adjacent to Z has other than amino, SH, CN or hydroxy as R';
(vii) Z is selected from the group consisting of O, NR, S, SO, $SO_2$, $PO_2R$ and POR;
(viii) wherein any carbon, when disubstituted, having as one substituent selected from the group consisting of hydroxy, amino, cyano and thiol, has the other substituent selected from the group consisting of hydrogen, alkyl, and aryl, whether this substituent is R' or R";

and to pharmaceutically acceptable salts of these compounds, stereoisomers and enantiomers thereof free from or mixed with other enantiomers or stereoisomers; and such compounds in compositions with a pharmaceutically-acceptable carrier thereof comprising a safe and effective amount of a subject skin lightening active.

10 Claims, 1 Drawing Sheet

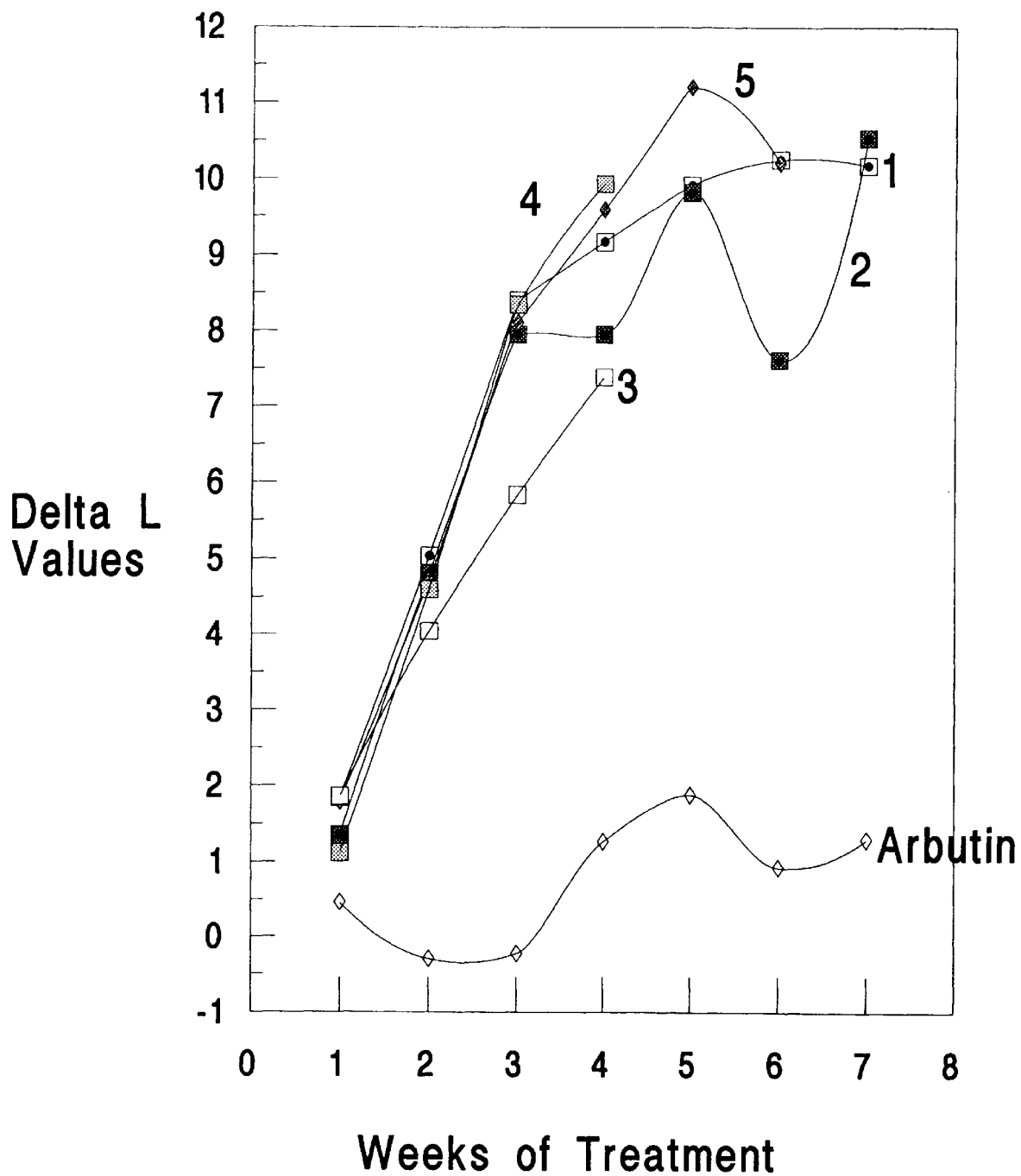

SKIN LIGHTENING COMPOSITIONS

This is a continuation-in-part of application Ser. No. 08/206,573, filed on Mar. 4, 1994, abandoned.

TECHNICAL FIELD

This invention relates to the field of skin lightening. Specifically, this invention relates to novel skin lightening compositions and methods of using the subject compositions to achieve skin lightening in mammals.

BACKGROUND OF THE INVENTION

Skin lightening is an important skin care need, especially in the Asian population. This includes overall lightening of basal skin tone and hyperpigmented regions. It is generally known that conditions which result in defective or missing tyrosinase, an enzyme involved in the formation of melanin lead to a loss of pigmentation, e.g. albinism. Conversely, it is known that inhibition of tyrosinase may likely lead to skin lightening via inhibition of melanogenesis. See King, R. A. and C. G. Summers, *Dermatologic Clinics,* Vol. 6 pp. 217–227 (1988).

Tyrosinase is present within the melanosomes in epidermal melanocytes and catalyzes the committed step in the formation of melanin from tyrosine. See Goldsmith, L. A., *Physiology, Biochemistry, and Molecular Biology of the Skin,* Oxford University Press, pp. 873–903 (N.Y. 1991). Tyrosinase catalyzes the hydroxylation of tyrosine (as a tyrosine hydroxylase) and the oxidation of DOPA to DOPAquinone (as DOPA oxidase):

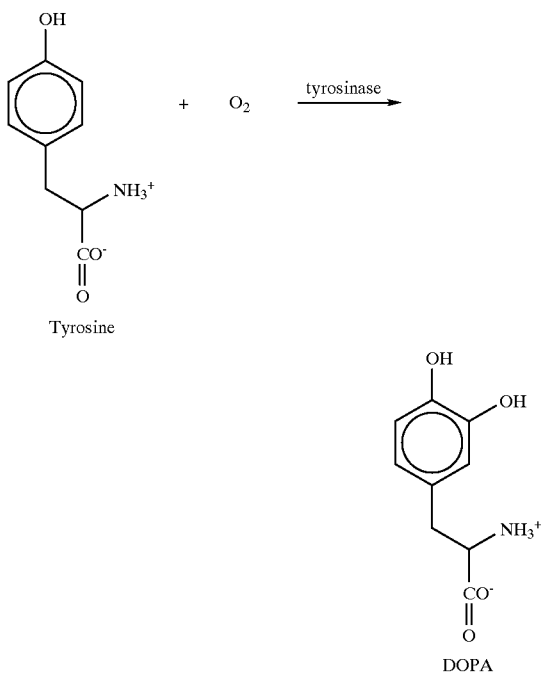

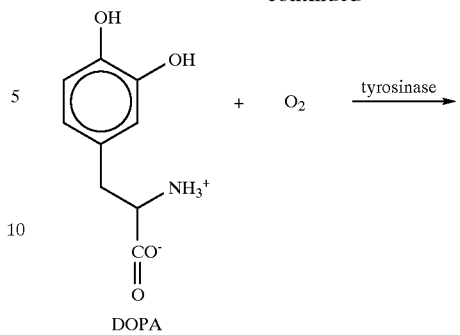

Binding of an inhibitor to the active site of tyrosinase results in decreased melanin formation. See generally Prota, G. *Melanins and Melanogenesis,* Academic Press, Inc., (San Diego 1992). The art has produced certain tyrosinase inhibitors. However, it is well recognized in the art that any active in any composition, especially when used for topical application (whether for pharmaceutical or cosmetic purposes) must be efficacious, bioavailable, stable when exposed to light, air or to the skin. Should the product be unstable, the breakdown products of the active must be innocuous.

Currently, there are several tyrosinase inhibitors in the marketplace, including hydroquinone, kojic acid and arbutin. However, there are disadvantages to each of these products.

For example, kojic acid and arbutin are marginal tyrosinase inhibitors and also are not very bioavailable, thus they have marginal efficacy.

Another example, hydroquinone, is oxidized by air, light and tyrosinase itself These oxidized products of hydroquinone have been implicated in skin irritation (and perhaps cytotoxicity) and in pigmentation rebound (i.e. initial lightening followed by darkening).

Therefore there is a need to provide a more effective skin lightening agent which is more efficacious than kojic acid or arbutin. In addition, there is a need to provide a stable tyrosinase inhibitor, which is resistant to oxidation from light, air, and tyrosinase, thus avoids the formation of by-products which can lead to skin irritation. The advantages of these more bioavailable and efficacious inhibitors are a noticeable lightening benefit with a lack of skin irritation. Other likely benefits will include ease of use, improved shelf life and decreased frequency of application. It is the object of this invention to provide such compounds and compositions.

SUMMARY OF THE INVENTION

This invention relates to compounds and compositions which achieve skin lightening in mammals and to their methods of use. These compounds and compositions provide compositions that have stability against oxidation and provide a stability advantage over many existing compositions. In addition, we have found that these compounds and compositions inhibit tyrosinase better than many prior art compounds and compositions and also are more bioavailable, thus they are more efficacious than the prior art.

Specifically, this invention relates to compositions and compounds for lightening skin having the structure:

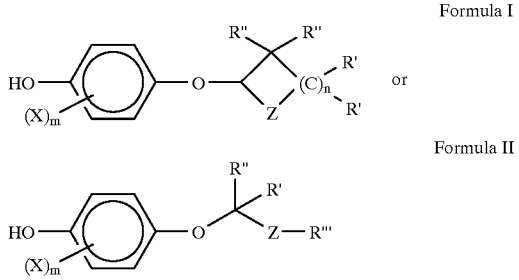

wherein:
(i) each X is, independently, selected from the group consisting of halo, alkyl, substituted alkyl, aryl, OR, OCOR, COR, CONRR, COOR, CN, SR, SOR, $SO_2R$, $SO_3R$ and NRR, wherein X is other than hydroxy, amino and thio, if this X is attached ortho to the phenol hydroxy;
(ii) m is an integer from 0 to 4;
(iii) each R' and each R" is, independently, selected from the group consisting of hydrogen, halo, alkyl, substituted alkyl, aryl, OR, OCOR, OCRROR, COR, CR(OR)OR, CONRR, COOR, CRROR, CN, SR, and NRR; wherein halo, when it appears, is other than geminal to a hydroxy, $NH_2$, or SH;
(iv) R''' is alkyl or substituted alkyl; wherein when R''' is present and R' is also hydrogen, R" is other than hydrogen, hydroxy, halo, thio, cyano and amino;
(v) each R is, independently, selected from the group consisting of hydrogen, alkyl, substituted alkyl and aryl;
(vi) n is an integer from 1 to about 5, wherein at least one carbon in (C)n has other than alkyl or hydroxy as a substituent, adjacent to Z has other than amino, SH, CN or hydroxy as R';
(vii) Z is selected from the group consisting of O, NR, S, SO, $SO_2$, $PO_2R$ and POR;
(viii) wherein any carbon, when disubstituted, having as one substituent selected from the group consisting of hydroxy, amino, cyano and thiol, has the other substituent selected from the group consisting of hydrogen, alkyl, and aryl, whether this substituent is R' or R".

Specifically included in this invention are pharmaceutically acceptable salts of these compounds, stereoisomers and enantiomers thereof free from or mixed with other enantiomers or stereoisomers and such compounds in compositions with a pharmaceutically-acceptable carrier thereof This invention further relates to methods of lightening skin in mammals by administering to the skin of a mammal a composition comprising a safe and effective amount of a subject skin lightening active.

DETAILED DESCRIPTION OF THE INVENTION

We have unexpectedly found that the compounds and compositions of this invention lighten skin in mammals. Furthermore, we have unexpectedly found that these compounds have improved stability toward oxidation, and are more bioavailable and efficacious than the prior art.

This invention is not limited to any particular mechanism of action, but is believed to operate by the inhibition of tyrosinase, an enzyme crucial for the formation of melanin. In this mechanism, the bioavailablity of the active compound and its inhibition of tyrosinase are predictive of efficacy.

As used herein, "alkyl" means carbon-containing chains which may be straight, branched or cyclic; substituted or unsubstituted; saturated, monounsaturated (i.e. one double or triple bond in the carbon chain), or polyunsaturated (i.e. two or more double bonds in the carbon chain, two or more triple bonds in the carbon chain, one or more double and one or more triple bonds in the carbon chain). Unless otherwise indicated, alkyl are preferably as follows. Preferred alkyl are straight or branched chain, more preferably straight chain. Preferred alkyl are mono-, di-, or tri- substituted, or unsubstituted, most preferably unsubstituted. Preferred alkyl are saturated or monounsaturated and, if so, preferably with a double bond; more preferably alkyl are saturated. Preferred alkyl are $C_1$–$C_{10}$, more preferably $C_1$–$C_4$, also more preferably methyl, ethyl and t-butyl, more preferably still methyl and ethyl, most preferably methyl.

Thus the term "substituted alkyl" is included in the definition of alkyl. Preferred alkyl substituents (i.e. substitution on alkyls) include halo, aryl, amino, hydroxy, alkoxy, cyano, nitro, amino (including mono- and disubstituted amino) thiol and substituted thiol and trifluoromethyl. More preferred alkyl substituents are halo and aryl. Thus "haloalkyl" is included in "alkyl" and includes, but is not limited to, trifluoromethyl, 1,1,1-trifluoroethyl, 1-chloroethyl, 3-chloropentyl, bromomethyl and the like.

As used herein the term "alkoxy" includes the above described alkyl radicals attached to the molecule via oxygen. Thus alkyl not only includes the $C_1$–$C_{10}$ alkyloxy, but also includes species such as methylenedioxy, ethylenedioxy and other similarly bifunctional, or multifunctional alkoxy substituents. These multifunctional substituents can be attached to various places in the molecule and thus form bridged species. For example, species such as dioxolanes, dioxanes and the like are specifically contemplated.

As used herein "halo" means F, Cl, Br, and I. Preferred "halos" are F, Cl, and Br, more preferably F and Cl, most preferably F.

As used herein, "aryl" means aromatic rings which may be unsubstituted or substituted. Preferred aryl are phenyl or naphthyl, especially phenyl. Preferred aryl are mono-, di-, tri- substituted or unsubstituted; more preferred aryl are monosubstituted or unsubstituted, most preferred being unsubstituted. Preferred aryl substituents include alkyl, halo, amino, hydroxy, alkoxy, cyano, nitro and trifluoromethyl. More preferred aryl substituents are alkyl and halo. The most preferred aryl is unsubstituted and thus is phenyl.

As used herein, the naming of any element, atom or radical contemplates all isotopes thereof Therefore, hydrogen includes deuterium, and tritium and similarly hydro, includes deutero, and the like.

As used herein, "pharmaceutically-acceptable salts" include $Na^+$, $K^+$, $Ca^{++}$, $Mg^{++}$, $Al_2(OH)_5^+$, $NH_4^+$, $(HOCH_2CH_2)_3NH^+$, $(CH_2CH_2)_3NH^+$, $(CH_3CH_2)_4N^+$, $C_{12}H_{25}(CH_3)_3N^+$ and $C_{12}H_{25}(C_5H_4N)_3N^+$ and the like. It is understood from this definition that some salts may include surfactants as the counterion. Preferred salts include $Na^+$, $K^+$, $NH_4^+$, and $(HOCH_2CH_2)_3NH^+$. More preferred salts include $Na^+$ and $NH_4^+$.

As used herein, "topical application" means directly laying on or spreading on outer skin.

As used herein, "pharmaceutically-acceptable" means that salts, drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically acceptable carrier utilized, and like factors within the knowledge and expertise of the attending physician.

As used herein "hyperpigmented region" means a localized region having high melanin content. Examples of these include, but are not limited to age spots, melasma, chloasma, freckles, post inflammatory hyperpigmentation, sun-induced pigmented blemishes and the like.

As used herein, "skin lightening" means decreasing melanin in skin, including one or more of; overall lightening of basal skin tone, lightening of hyperpigmented regions including age spots, melasma, chloasma, freckles, post inflammatory hyperpigmentation or sun-induced pigmented blemishes.

As used herein, "skin lightening agent" means an active agent, or a pharmaceutically-acceptable salt thereof, as defined herein below.

As used herein, all percentages are by weight unless otherwise specified.

Simple chemical transformations which are conventional and well known to those skilled in the art of chemistry can be used for effecting changes in functional groups in the compounds of the invention. For example, acylation of hydroxy- or amino-substituted species to prepare the corresponding esters or amides, respectively; preparation of ethers, including methyl and benzyl ethers, or cleavage of methyl or benzyl ethers to produce the corresponding alcohols or phenols; and hydrolysis of esters or amides to produce the corresponding acids, alcohols or amines; aromatic substitution, including halogenation of aromatic rings, etc.; oxidation of alcohols to ketones, acids or aldehydes; and other reactions, as desired, can be carried out.

Active Agent

This invention involves the lightening of mammalian skin by administering to the skin a safe and effective amount of a compound having the structure:

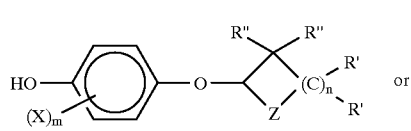

Formula I or

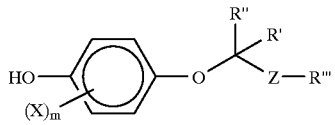

Formula II or a pharmaceutically-acceptable salt thereof.

In the above structures each X is, independently, selected from the group consisting of halo, alkyl, aryl, OR, OCOR, COR, CONRR, COOR, CN, SR, SOR, $SO_3R$, $SO_2R$ and NRR; each X is preferably independently selected from the group consisting of halo, alkyl, haloalkyl, substituted alkyl, OR and OCOR; more preferably from the group consisting of F, Cl, Br, methyl, OH, $OCH_3$ and $OCOCH_3$.

In addition, where X is SH, $NH_2$ or OH and is attached to the carbon ortho to the phenolic hydroxy, and such substituents render the molecule more prone to oxidation (a problem common to some prior art compounds) and thus species with these substituents when in this arrangement are not contemplated to be part of the invention, if they result in an unstable active.

In the above structures, each R is, independently, selected from the group consisting of hydrogen, alkyl, substituted alkyl and aryl; preferably hydrogen or alkyl.

In the above structures, m is an integer from 0 to 4; preferably 0 to 2; more preferably 0 or 1. Of course, when m is 0, then the aryl ring is unsubstituted.

In the above structures, each R" and R' is, independently, selected from the group consisting of hydrogen, halo, alkyl, substituted alkyl, aryl, OR, OCOR, OCRROR, COR, CONRR, CRROR, COOR, SR, NRR, and CN.

R' is preferably from the group consisting of hydrogen, halo, haloalkyl, aryl, and alkyl. In compounds of formula I, R' is more preferably $C_1$ to $C_3$ alkyl, hydroxy, halo, cyano or hydrogen, and still more preferably H, F, Cl, Br or methyl. In compounds of formula II, R' is preferably hydrogen or alkyl, more preferably hydrogen.

R" is preferably from the group consisting of hydrogen, halo, alkyl, haloalkyl, substituted alkyl, OR and OCOR; in compounds of formula I, more preferably from the group consisting of H, F, Cl, Br, methyl, OH, $OCH_3$ and $OCOCH_3$; in compounds of formula II, R" is preferably $C_1$ to $C_3$ alkyl or $C_1$ to $C_3$ alkyl substituted with methoxy, acetoxy, hydroxy, chloro, fluoro, or bromo.

For compounds of formula I; less than about four R' and R" are other than hydrogen, preferably less than three, most preferably up to two. In this case the most preferred substituents are hydroxy, halo, cyano and alkyl. However, in this case hydroxy, thiol cyano or any other substituents which will render the molecule unstable, these are not attached to the same carbon as Z. It is preferred that R' is alkyl, substituted alkyl, alkoxy or hydrogen for R' attached to the carbon adjacent to Z in the ring.

Thus it is apparent that certain radicals are not intended to be arranged to describe an inherently unstable molecule. The skilled artisan will immediately recognize that, certain substituents are specified so as not to appear in certain specific arrangements for this reason. For example, where any carbon has geminal hydroxy substituents, or a hydroxy and $NH_2$, or hydroxy and SH, or geminal SH or geminal $NH_2$, and such compounds are inherently unstable, these compounds and their compositions are not contemplated to be part of the invention. Likewise, where alpha-halo hydroxy and the like render the species inherently unstable, this species is not contemplated to be a part of the invention.

However, bearing these considerations in mind, it is understood by the skilled artisan that species are not inherently unstable (i.e. are stable) if they remain reasonably resistant to degradation in a composition on the shelf and in delivery or application.

In the above structures, n is an integer from 1 to 5; preferably 2 or 3.

In the above structures, Z is selected from the group consisting of O, NR, S, SO, $SO_2$; POR and $PO_2R$; more preferably O or S.

In the above structures, R''' is alkyl or substituted alkyl; preferably unsubstituted alkyl or alkyl substituted with halo, aryl, COR, CONRR, hydroxy, or alkoxy; more preferably methyl, $CF_3$ or $C_1$–$C_4$ alkyl substituted with F, Cl, Br, $CF_3$ or $OCH_3$.

The compounds of the invention are useful both in the form of the active itself and the form of salts of the active (i.e., cosmetically or pharmaceutically acceptable salts), and both forms are within the purview of the invention. The salts may be in some cases a more convenient form for use, and in practice the use of the salt form inherently amounts to the use of the active itself In addition to convenience, the salt may aid in dissolution, topical delivery and the like of the active. The preferred moieties which can be used to prepare the salts include those which produce, when combined with the free base, pharmaceutically or cosmetically acceptable salts, that is, salts whose counterions are relatively innocuous to the animal organism in common doses of the salts so that the beneficial properties inherent in the free form are not vitiated by side effects ascribable to the counterion. Appropriate acceptable salts within the scope of the invention are those derived from other mineral acids and organic acids or mineral bases and organic bases, depending upon the pKa of the active. Here bases, as described above, are preferred in preparation of the salt. These salts are prepared in conventional ways, for example, by dissolving the free molecule in aqueous alcohol solution containing the appropriate counterion or counterion precursor (e.g. an unprotonated base or protonated acid; which are not ionized and thus soluble) and then isolating the resulting salt by evaporating the solution, or by reacting the free molecule and a counterion or counterion precursor in an organic solvent, in which case the salt separates directly, is precipitated with a second organic solvent, or can be obtained by concentration of the solution; other methods exist. All salts are useful as sources of the free form of the active, even if the particular salt per se is desired only as an intermediate product, as, for example, when the salt is formed only for purposes of purification, identification, or when it is used as an intermediate in preparing a medicinally acceptable salt by ion exchange procedure, or as a means to purify an enantiomer or stereoisomer.

It is recognized that the compounds of the invention can exist as stereoisomers, and as such the description of the compounds includes all stereoisomers and mixtures thereof. Furthermore, it is understood that the skilled practitioner can selectively prepare the desired stereoisomer, using selective synthetic methods. These methods include (but are not limited to) temperature control (to prepare kinetic vs thermodynamically favored products), selective catalysts and/or chiral solvents (which encourage the preparation of one stereoisomer over another, even in prochiral molecules), chiral auxilliaries, the choice of specific reactions, and the like. It is also recognized that methodologies exist for the separation of chiral mixtures including (but not limited to) preparation of a salt using a chiral counterion (for example, tartrate and other chiral anions or cations), use of a chiral solvent (for example sec-butanol), use of stereoselective chromatography and the like. Such selection of stereoesomers is often advantageous as one stereoisomer can be more active than another. Thus it is within the scope of the invention to have mixtures of stereoisomers as well as one or more stereoisomer(s) substantially free of the other stereoisomer(s). For example, it is known that one stereoisomer of one of the compounds of this invention inhibits tyrosinase better than the other stereoisomer, and thus it is sensible and contemplated that a practitioner might prefer to treat the mammal in need of treatment with the stereoisomer which inhibits tyrosinase better, all other properties being equal.

In addition, it is recognized that the compounds of the invention exist as enantiomers. Since the same considerations apply to enantiomers as stereoisomers, it is expected that a practitioner might prefer to treat the mammal in need of treatment with the enantiomer which inhibits tyrosinase better, all other properties being equal. Thus it is within the scope of the invention to have a mixture of enantiomers as well as one enantiomer substantially free of the other enantiomer.

It is also apparent that making minor changes in the reaction's conditions leading to the desired product is within the purview of the skilled artisan in organic chemistry. For example, adjusting temperature/pressure of a reaction, adjusting workup conditions to maximize recovery of the desired material, increased time for reaction and the like, are strategies employed to increase yield and are often not crucial to the successful synthesis of the desired molecule. In addition, the selection of preferred reactants in any given reaction is generally a matter of selection, for example, the choice of one acid over another, when used to protonate a reactant, is neither crucial to the successful synthesis, nor outside the purview of the skilled artisan.

In the methods of preparing compounds of the invention below, or elsewhere, any carbon with clearly undesignated substitution has the appropriate number of hydrogens.

Compounds with cyclic heterocycles, wherein Z is oxygen are conveniently prepared by the enol-ether synthesis as illustrated below;

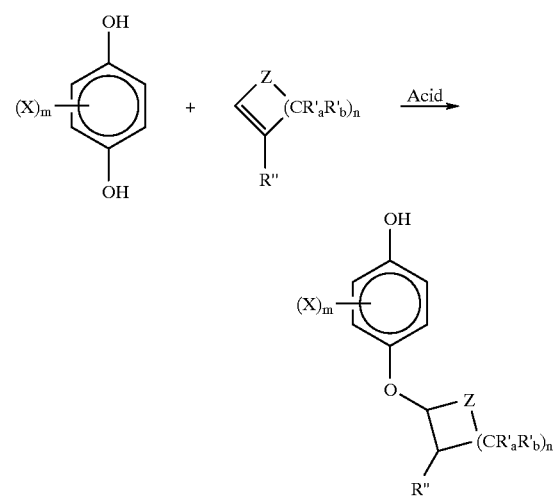

In addition, variations in stereochemistry can be effected by utilizing various synthetic methods. For example an α,β epoxide of pyran, prepared in situ, can be reacted (or trapped) under electrophilic conditions to prepare a trans-hydroxy compound. The trans-oxycyclic actives having hydroxy, methoxy, acyloxy and the like can be prepared by analogy to the following method;

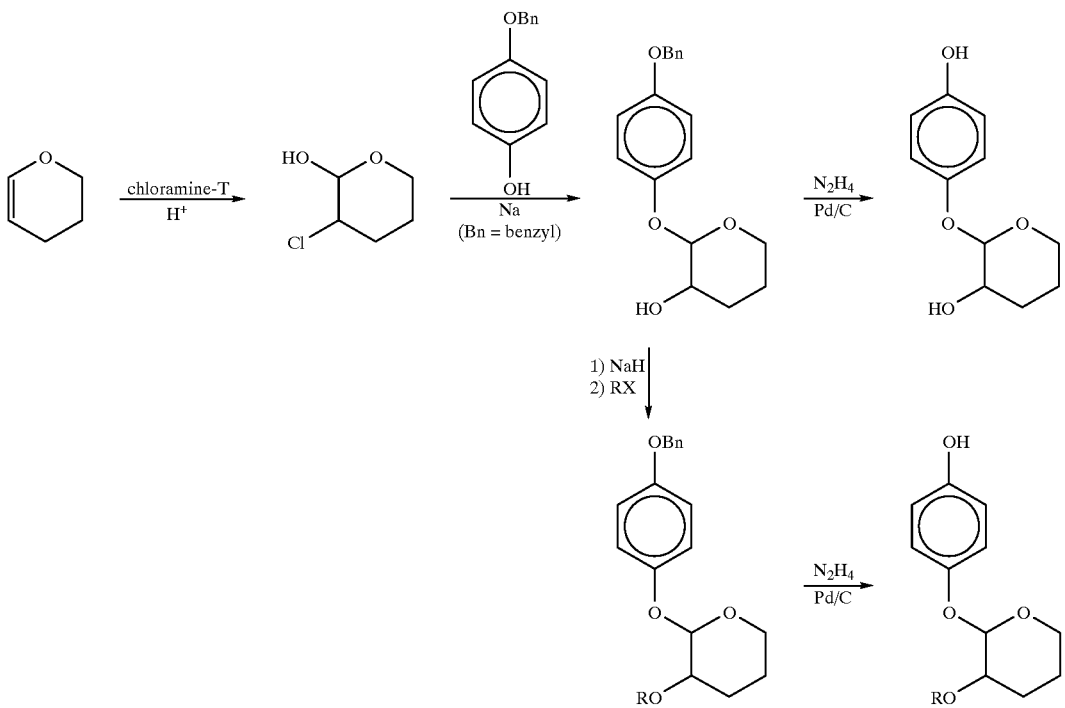

The analogous cis-oxycylic compounds are prepared by oxidation/reduction of the trans compound. It is contemplated that the selective synthesis is performed and prescribed by the desired end product to be used as an active. Of course, rings of other types and sizes can be manipulated using similar methods with different starting materials.

Preparation of the compounds with heterocycles wherein Z is NR are prepared by known methods (Cf Hanessian, S. (1965) Chemistry and Industry 1296–1297; Heathcock, C. H., Norman, M. H., and Dickman, D. A. (1990) J. Org. Chem. 55, 798–811; Shono, T., Matsumura, Y., Onomura, O., and Yamada, Y. (1987) Tetrahedron Letters 28 4073–4074) and by methods analagous to those of compounds wherein Z is O.

Compounds with heterocycles wherein Z is sulfur can be prepared by analogy to the method of Giovani, E. Napolitano, E., and Pelosi, P. (1993) Gazzetta Chimica Italiana 123, 257–260. The resulting thioethers can then be oxidized to sulfoxides and subsequently to sulfones using known oxidizing reagents, such as peroxides, PCC, $KMnO_4$ and the like.

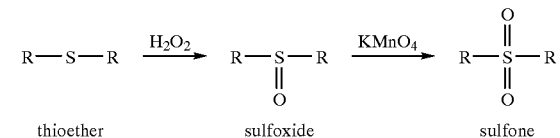

Compounds with Z=$PO_2R$ and POR are prepared by analogy to known chemistries (Cf Inokawa, S., Kitagawa, H., Kuniaki, S., Hiroshi, Y., and Ogata, Y. (1973) Carbohydrate Research 30, 127–132; Hanaya, T., Nobuyuki, S. Yamamoto, H., Armour, M-A., and Hogg, A. M. (1990) Bull. Chem. Soc. Jpn. 63, 421–427) Starting materials chosen to prepare these compounds of the invention, are known, or are prepared by known methods. Once the materials are chosen, such compounds are prepared and manipulated by known chemistries.

Compounds with acyclic groups are prepared by several methods; preferred methods for preparing compounds with R' as hydrogen and Z as O or S include;

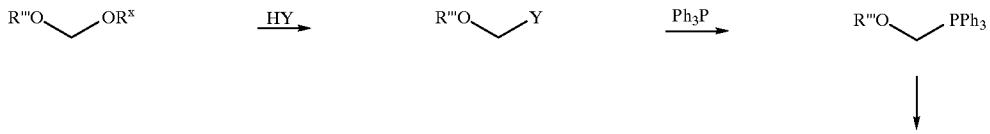

-continued

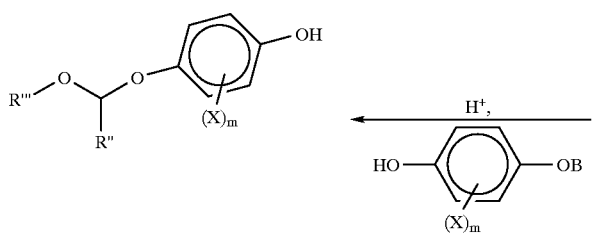 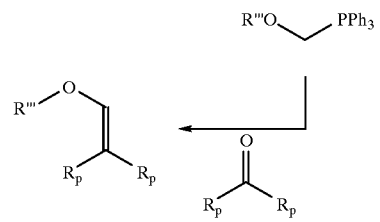

wherein $OR^x$ is a group that can be displaced by an anion, B is a blocking group, Y is a leaving group and Ph is aryl, and where each Rp independently is a precursor to R", such that R" is CRpRp.

Other vinyl ethers and thio vinyl ethers are prepared by several known methods, for example, by reactions of ketones, or aldehydes with Wittig reagents and the like. Many vinyl ethers and thioethers are known or commercially available, and these are also expected to be useful in the final reaction step above thus producing the desired active product.

Compounds wherein R" is methyl are prepared by the following scheme as well;

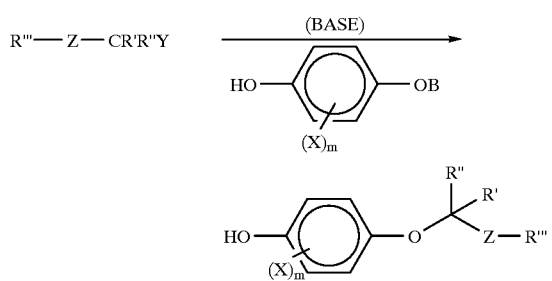

where Y is a leaving group, including tosyl, halo, and the like.

Where Z is O, NR or S, a method analogous to the following is employed to prepare the compounds of the invention:

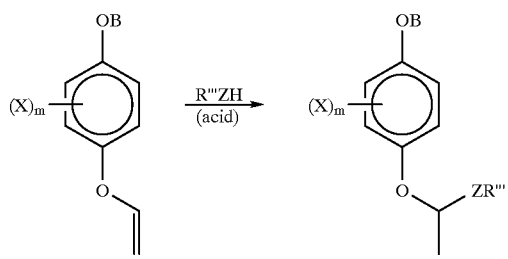

This synthesis is useful for nearly any R'". Where R" is hydroxymethylene a method analogous to the following scheme is preferred;

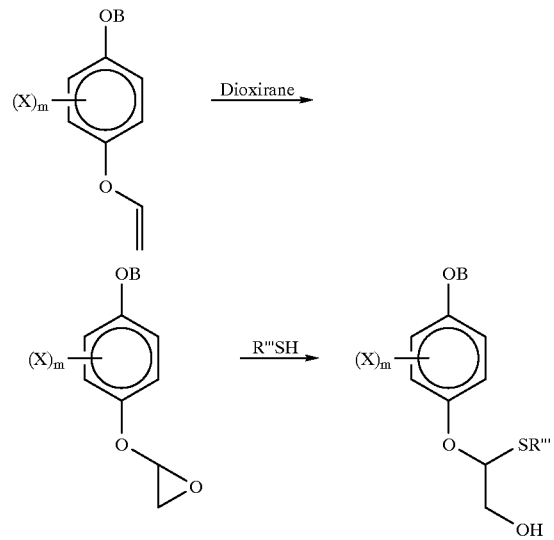

Other epoxidation agents can be used in the first step, including m-chloroperbenzoic acid (MCPBA) and the like. Where Z is O or NR, compounds are prepared by analogy to the preceding scheme;

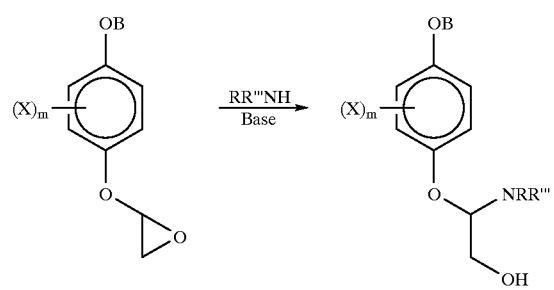

Where RR'"NH is any secondary amine in the presence of a strong base.

Of course, blocking and unblocking of phenolic hydroxy (using groups designated B above) and the like are done by art recognized methods, such as using the benzyl group, and later reducing the group off with palladium on carbon and the like.

The structures of the compounds of the invention are established by the mode of synthesis, by elemental analysis, and by infrared, nuclear magnetic resonance, or mass spectroscopy. The course of the reactions and the identity and homogeneity of the products are often assessed by thin layer chromatography (TLC) and high pressure liquid chromatography (HPLC) and melting point.

Once prepared, the tyrosinase inhibition activity of the active compound is determined by standard enzyme kinetic methods. The in vitro determination of a $K_i$ value is a well accepted parameter to judge the strength of a compound's inhibition of an enzyme. The art describes assays which show inhibition of tyrosinase by other molecules, but these assays are inherently insensitive and typically inaccurate.

An improved tyrosinase assay combining the resolution of HPLC and the sensitivity of fluorescence detection is developed to provide a more reproducible and sensitive measurement of tyrosinase activity and inhibition. In this assay, concentrations of tyrosine, DOPA, and tyrosinase are optimized to determine the kinetic parameters of tyrosinase. The assay measures conversion rates of tyrosine to 3,4-dihydroxyphenylalanine (DOPA) catalyzed by tyrosinase (i.e. tyrosine hydroxylase activity). HPLC separates tyrosine from other assay components to provide reproducible substrate quantitation. HPLC-fluorescence detection provides quantitation of concentrations of tyrosine to as low as 0.1 $\mu$M tyrosine and changes in concentration smaller than 0.1 $\mu$M. This improved assay reliably determined the strength of inhibition ($K_i$) as well as the type of inhibition (i.e. competitive vs. noncompetitive inhibition) of enzyme inhibitors with excellent reproducibility and sensitivity. This assay allows for the quantitative comparison of known tyrosinase inhibitors and novel compounds.

Tyrosinase is commercially obtained. Kinetic assays to determine the strength ($K_i$) and type of inhibition of inhibitors are performed as described and summarized. Inhibitors at varying concentrations (from nanomolar to millimolar) are incubated in the presence of tyrosine (1–50 $\mu$M) and tyrosinase (2U/mL) in 100 mM of pH 7.0 MOPS buffer containing 0.5 $\mu$M DOPA. The samples are analyzed at times 0, 6, 12, 18, and 24 min by HPLC chromatography (using a Supelco cyano analytical column) for the depletion of tyrosine. A fluorescence detector ($\lambda_{excit}$=260 nm $\lambda_{emis}$=305 nm) is used to detect tyrosine. The $K_i$ values and type of inhibition are determined from graphic analysis of data using the accepted Lineweaver-Burke and Dixon plots. The inhibition values for preferred compounds (i.e. the $K_i$ values) are determined by standard methods and showed good to excellent tyrosinase inhibition.

The actives are tested for oxidation by tyrosinase, and none are appreciably oxidized by tyrosinase.

Actives are tested in solution and composition for stability, including stability toward light, air, and water. None of the actives tested showed appreciable oxidation by air or light. Based upon these results, it is shown that stable formulations could be prepared where the active is not appreciably oxidized by air or light.

Skin penetration values (Jmax) are predicted for each example compound from the flux equation as described by Kasting, et al., 1992. Jmax is defined as the flux of a moderately lipophilic solute across the skin from vehicle. The compound's parameters (e.g., melting point, molecular weight, clog p (calculated partition coefficient)) are used to calculate the flux value as written:

$$\text{Jmax}=(D_{lip}/h_{lip})*S_{lip}$$

where Jmax is the maximum flux through the barrier ($\mu$g/cm$^2$/h)

$h_{lip}$ is the effective thickness of the stratum corneum lipid barrier (cm)

$D_{lip}$ is the diffusion coefficient of the drug in this barrier (cm$^2$/h)

$S_{lip}$ is the solubility of the drug in this barrier (pg/cm$^3$)

This model predicts penetration of compounds through skin. In fact, compounds of the invention are predicted to be more bioavailable than arbutin and kojic acid based on this parameter (Jmax). Thus the actives are predicted to be efficacious without the common drawbacks associated with prior art compounds such as oxidation, lack of bioavailability, or poor tyrosinase inhibition. Preferred compounds have Jmax of 2 $\mu$g/cm$^2$/h or greater, when used topically.

Preferred compounds (which are predicted to penetrate skin well and displayed excellent tyrosinase inhibition) are tested in the pigmented guinea pig, an art accepted model for skin lightening efficacy, to determine their in vivo efficacy in a composition. On each guinea pig from two to six treatment sites (typically 16 cm$^2$ each) are treated topically with compositions containing preferred compounds (100 $\mu$L of 0.1–3% active, 5× per week for up to 6 weeks). The animals are visually and instrumentally graded with a Minolta Chromameter (CR-300) for erythema (i.e., a redness scale using "a" values) and pigmentation (i.e., a lightness scale using "L" values). Each week the treatment sites on the animals are also photographed. By both visual and instrumental methods, the compounds tested in vivo lightened skin, without appreciable irritation or pigmentation rebound.

Based on results above it is believed that skin lightening compositions of this invention preferably comprise from about 0.001% to about 10% of a subject active compound in a topical composition, more preferably from about 0.01% to about 8%, more preferably still from about 0.1% to about 5%, most preferably from about 0.5% to about 5% of an active compound. Use of subject compositions comprising at least 5% of an active is preferred for lightening of hyperpigmented regions and other areas where substantial lightening is desired.

Preferred compounds of the invention include;

Example Ia

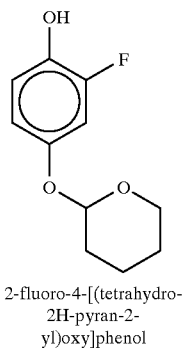

2-fluoro-4-[(tetrahydro-2H-pyran-2-yl)oxy]phenol

Example IIa

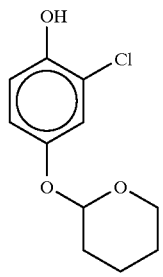

2-chloro-4-[(tetrahydro-2H-pyran-2-yl)oxy]phenol

-continued

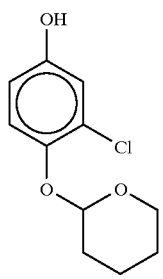

3-chloro-4-
[(tetrahydro-2H-pyran-
2-yl)oxy]phenol

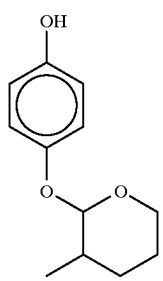

4-(3-methyltetrahydro-
2H-pyran-2-yl)phenol

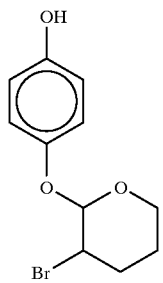

4-(3-bromotetrahydro-
2H-pyran-2-
yl)oxyphenol

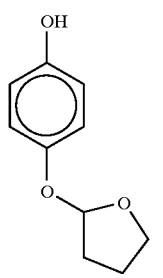

4-[(tetrahydrofuran-2-
yl)oxy]phenol

Example IIb

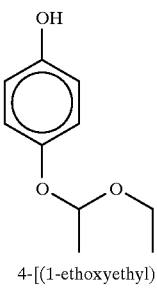

4-[(1-ethoxyethyl)
oxy]phenol

Example IIc-d

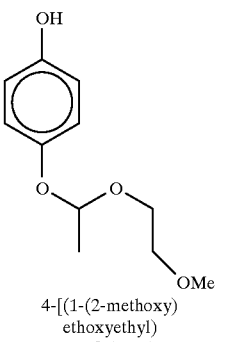

4-[(1-(2-methoxy)
ethoxyethyl)
oxy]phenol

Example III

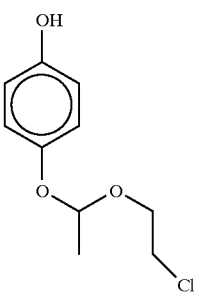

4-[(1-(2-
chloro)ethoxyethyl)
oxy]phenol

Example IVa

Example IVb

Example IVc

Example IVd

Example Va

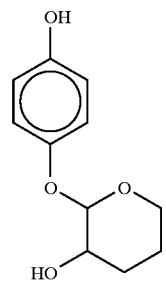

4-(3-hydroxy-
tetrahydro-2H-pyran-2-
yl)phenol

-continued

Example VI

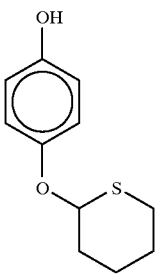

4-[(tetrahydro-2H-
thiopyran-2-
yl)oxy]phenol

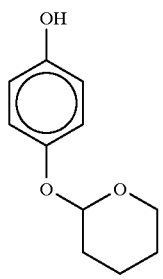

4-[(tetrahydro-2H-
pyran-2-yl)oxy]phenol

The most preferred compounds of this invention include; 4-[(tetrahydro-2H-pyran-2-yl)oxy]phenol; 4-[(tetrahydro-2H-thiopyran-2-yl)oxy]phenol; 2-fluoro-4-[(tetrahydro-2H-pyran-2-yl)oxy]phenol; 4-[(tetrahydrofuran-2-yl)oxy]phenol; and 4-[(1-ethoxyethyl)oxy] phenol .

The compounds of the invention are prepared by conventional methods using known starting materials. However, it is readily apparent to the skilled practitioner in organic chemistry that certain starting materials may be novel, but are made by methods which are known in the art. Moreover, the skilled artisan will recognize that some reactions are best performed by blocking functional groups on the reactants that may engage in undesirable side reactions. The recognition of the possibility of such reactions, the selection of blocking moieties to protect functional groups and the optimization of reactions with or without such groups is well within the purview of the skilled artisan.

The following examples are provided to further illustrate the invention, while not limiting the invention hereto:

SYNTHESIS OF EXEMPLARY COMPOUNDS

The following examples are illustrative of the preparation of compounds useful in this invention.

EXAMPLE Ia 2-fluoro-4-[(tetrahydro-2H-pyran-2-yl)oxy] -phenol

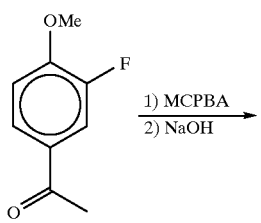

-continued

Example VII

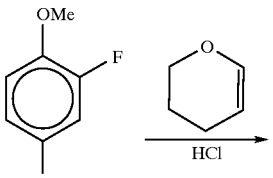

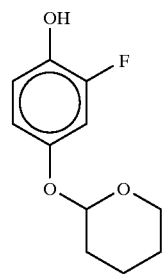

Step 1 3-Fluoro4-methoxyphenol

A stirred solution of 3'-fluoro-4'-methoxyacetophenone (5.0 g, 29.7 mmol), m-chloroperoxybenzoic acid (~50%) (12.8 g, 37.1 mmol), and CH$_2$Cl$_2$ (150 mL) is heated at reflux for 48 h, at which time TLC analysis (CH$_2$Cl$_2$ on silica gel) indicated a substantial amount of starting acetophenone is present. An additional portion of m-chloroperoxybenzoic acid (~50%) (2.0 g, 5.8 mmol) is added followed by 18 h of reflux. At this point no starting material remained. The reaction mixture is cooled then washed with 5% aqueous K$_2$CO$_3$ (3×200 mL). The washed organic layer is concentrated in vacuo to an oil which is dissolved in EtOH (18 mL). To the resulting solution is added 5% aqueous NaOH (5 g). the resulting mixture is stirred at room temperature for I h, at which time TLC analysis (CH$_2$Cl$_2$ on silica gel) indicated complete disappearance of ester. This residue is dissolved in deionized H$_2$O (50 mL), washed with Et$_2$O (50 mL), then adjusted to ~pH 4 by the addition of concentrated hydrochloric acid. The aqueous mixture is extracted with Et$_2$O (3×30 mL). The organic layers are combined, washed with deionized H$_2$O (2×10 mL), dried over Na$_2$SO$_4$, then concentrated in vacuo to give 4.1 g (97.2%) of product. An additional 10 g of 3'-fluoro-4'-methoxyacetophenone is reacted in a similar manner to give a total of 11.5 g (92.5%) of product which is chromatographed on silica gel eluted with CH$_2$Cl$_2$ (2.0 L). Pure fractions are combined, filtered, then concentrated in vacuo to give a product suitable for further transformation.

Step 2 2-[(3 -Fluoro4-methoxy)phenoxy]tetrahydropyran

To a stirred solution of 3-fluoro-4-methoxyphenol (9.2 g, 64.7 mmol), concentrated hydrochloric acid (1 drop), and CH$_2$Cl$_2$ (180 mL) is added a solution of 3,4-dihydro-2H-pyran (7.7 g, 91.6 mmol in 50 mL of CH$_2$Cl$_2$) during 5 min. The reaction mixture is stirred at room temperature for 2 h, at which time TLC analysis (CH$_2$Cl$_2$ on silica gel) indicated disappearance of the phenol. The reaction mixture is washed with 4% aqueous NaOH (2×300 mL). The organic layer is dried over Na$_2$SO$_4$, then concentrated in vacuo to an oil which is co-distilled with hexanes (3×100 mL) to give an oil suitable for the next step.

Step 3 2-fluoro-4-[(tetrahydro-2H-pyran-2-yl)oxy]-phenol

To a stirred solution of 60% sodium hydride (4.18 g, 105 mmol) and N,N-dimethylformamide (180 mL) at 0° C. (ice bath) is slowly added (~5 min) ethanethiol (6.9 g, 110 mmol). The reaction mixture is stirred at room temperature for several min to form a clear solution, then 2-[(3-fluoro-4-methoxy)-phenoxy]tetrahydropyran (14.0 g, 61.9 mmol) is added in one portion. The reaction is heated to 140° C. and maintained at that temperature for 2 h at which time TLC analysis (hexanes/EtOAc, 4:1) on silica gel indicated completeness of reaction. The reaction mixture is cooled to ~50° C. then poured into saturated aqueous NH4Cl (1.8 L). The resulting mixture is extracted with Et$_2$O (3×1 L). The Et$_2$O extracts are combined, washed in succession with deionized water (1 L) and saturated NaCl (1 L), dried over Na$_2$SO$_4$, then concentrated in vacuo to an oil. This oil is chromatographed on silica gel eluted with hexanes/EtOAc (4:1) (10 L). Pure product fractions are combined, clarified, then concentrated in vacuo to give an amber oil which is triturated in hexanes (100 mL). The resulting crystalline solid is collected, washed with hexanes (50 mL), then dried in vacuo at room temperature to constant weight to give purified target compound.

EXAMPLES Ib–Ill

In addition, it is specifically contemplated that compounds, wherein X is halo, nitro, alkyl, aryl, acyl, formyl, alkoxy, cyano, sulfonyl, amino, thio, sulfonyl and the like and wherein m is between 1 and 4, are prepared using the methods described above, and any of the following commerically available compounds listed below are used to prepare compounds of the invention, using the method of the example above and substituting the following phenols. In addition, the functional groups in the aryl ring are able to be further manipulated to provide other functionality by known methods.

"A,B,C,and D" in this table refer to substituents on the aromatic ring, and thus fit within the definition of X elsewhere in the specification and in the claims. "W" in this table is a blocking group which can either be used to elaborate the starting material into the compound of the invention or to block side reactions (described above) and is removed during synthesis by conventional methods. Note that where a space exists in the table, this indicates that the position is unsubstituted and thus is hydrogen.

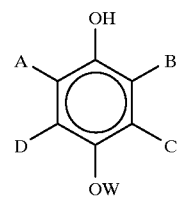

| Example | A | B | C | D | W |
|---|---|---|---|---|---|
| Ib | CH$_3$ |  | C |  |  |
| Ic | Br | Br |  |  |  |
| Id | NO$_2$ | NO$_2$ |  |  |  |
| Ie |  | H |  | OCH$_3$ | CH$_3$ |
| If |  | SO$^-_3$ |  |  |  |
| Ig |  | CH$_3$ |  | (—CH$_2$—COO—) |  |
| Ih |  | CH$_3$ |  |  |  |
| Ii |  |  |  | CH$_2$CO$_2$H |  |
| Ij | C$_6$H$_5$SO$_2$ |  |  |  |  |
| Ik | Benzotriazol-2-yl |  |  |  |  |
| Il | Cl |  |  |  |  |
| Im | OCH$_2$CH$_3$ |  |  |  |  |
| In | C$_6$H$_5$ |  |  |  |  |
| Io | CH$_3$CO |  |  |  |  |
| Ip | (CH$_3$)$_3$C |  |  |  |  |
| Iq |  |  |  | CH$_3$CH$_2$O | CH$_3$ |
| Ir | OCH$_3$ |  |  |  |  |
| Is | CH$_2$CH$_3$ |  |  |  |  |
| It | H$_2$N C(NH)S |  |  |  |  |
| Iu |  |  |  | NO$_2$ | CH$_3$ |
| Iv | Br |  |  |  |  |
| Iw |  |  |  | (—C(CH$_3$)$_2$CH(morph)O—) |  |
| Ix | NO$_2$ |  |  |  | CH$_3$ |
| Iy | Cl |  |  |  | CH$_3$ |
| Iz | F |  |  |  | CH$_3$ |
| Iaa | CN |  |  | CN |  |
| Ibb | CH$_3$ |  |  | CH$_3$ |  |
| Icc | CHO |  |  | Br | CH$_3$ |
| Idd | CH$_3$CH$_2$ |  |  | OCH$_3$ |  |
| Iee | C$_6$H$_5$ |  |  | CH$_2$CH$_3$ |  |
| Iff | CH$_3$CO |  |  | allyl |  |
| Igg | Cl |  |  | Cl | CH$_3$ |
| Ihh | CH$_3$ | CH$_3$ | C |  |  |
| Iii | Br | Br | Br | Br |  |

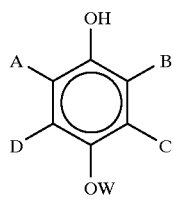

| Example | A | B | C | D | W |
|---------|---|---|---|---|---|
| Ijj | Cl | Cl | Cl | Cl | |
| Ikk | CH₃ | CH₃ | CH₃ | CH₃ | |
| Ill | OCH₃ | OCH₃ | OCH₃ | OCH₃ | |

EXAMPLE II

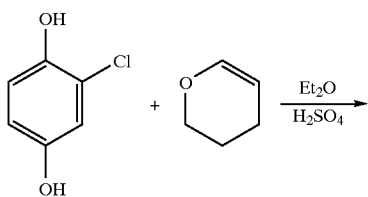

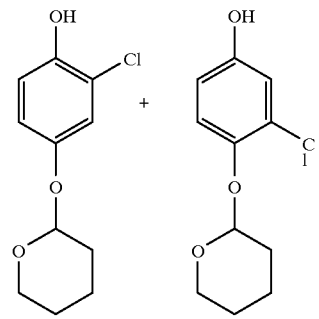

To a dry round bottom flask equipped with an argon inlet, is placed chlorohydroquinone (10.0 g; 69.2 mmol), 500 ml of diethyl ether, and 500 μl of concentrated sulfuric acid dissolved in 20 ml of diethyl ether. Next, 3,4-dihydro-2H-pyran (5.68 ml; 62.3 mmol) dissolved in 75 ml of diethyl ether is added dropwise over two hours. The solution is left stirring for one hour. Solid sodium carbonate is slowly added until the solution stops bubbling. The solution is vacuum filtered, washed three times with a saturated sodium chloride solution, and dried over magnesium sulfate. Next, the mixture is filtered, the filtrate is concentrated on a rotary evaporator, and the solution left in the freezer overnight. The mixture is chromatographed on a silica gel column using 9:1 hexanes:ethyl acetate as eluant. Appropriate fractions are combined, as determined by TLC, the solvent is evaporated using a rotary evaporator, and the products are dried in a high vacuum oven without heat. Anisaldehyde spray reagent is used to view the ethers by TLC, and the structures are confirmed by carbon and proton NMR. Both the 2-chloro compound (Example IIa) and the 3-chloro compound (Example IIb) are prepared in this synthesis.

The products are clear yellow oils.

EXAMPLE IIc–d

Using the appropriate starting material, the following compounds are prepared as a mixture and separated by chromatography;

| Ex | (X)m | Z | R" | [CR'ₐR'ᵦ]ₙ |
|----|------|---|-----|------------|
| IIc (cis)* | (X)o | O | CH₃ | CH₂CH₂CH₂ |
| IId (trans)* | (X)o | O | CH₃ | CH₂CH₂CH₂ |

*these stereoisomers have different tyrosinase inhibition activities ($K_i$) and different penetration properties ($J_{max}$).

EXAMPLE III

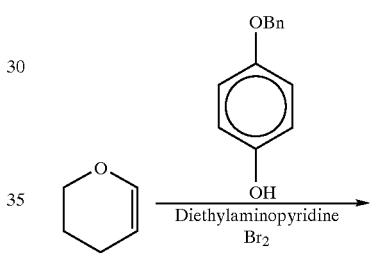

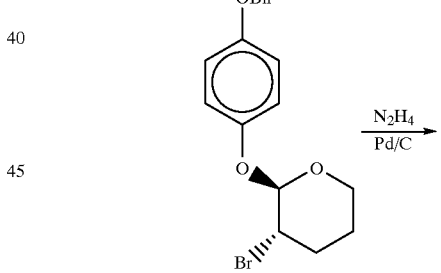

To a chilled (−78° C.) solution of dihydropyran (1.0 equiv.) in anhydrous methylene chloride is slowly added a solution of bromine (0.95 equiv.) in methylene chloride. N,N-diethylaniline (1.0 equiv.) is added after 15 minutes of stirring and the mixture warmed to 0° C. with an ice bath.

4-(Benzyloxy)phenol is then added in the form of a methylene chloride slurry, the ice bath removed and the reaction mixture stirred for at least 48 hours at room temperature under an inert atmosphere, whereupon the solvent is removed in-vacuo. Residue is extracted with diethyl ether, washed with sodium carbonate (10%) and dried over potassium carbonate. Volatiles are removed in-vacuo and the crude solid recrystallized from hot methanol to give the desired intermediate as a white solid.

To a stirred suspension comprising the benzyl protected intermediate (1.0 equiv.), 5% Pd/C (0.07 equiv.) and methanol is added 55% hydrazine hydrate (~20 equiv.). The reaction mixture is slowly heated and maintained at reflux under an inert atmosphere until TLC analysis indicates complete consumption of starting material. Reaction mixture is cooled to room temperature, filtered through celite to remove catalyst and volatiles removed in-vacuo. Residue is then subjected to low pressure column chromatography with 7:3 hexane:ethyl acetate as eluent. Composition and purity of isolated white solid as determined by $^1$H and $^{13}$C NMR is consistent with the brominated compound shown. (Removal of 4-[(tetrahydro-2H-pyran-2-yl)oxy]phenol by-product, if necessary, is achieved via selective acid hydrolysis in a pH 5 buffer solution, extraction into chloroform, cooled to room temperature, filtered through celite to remove catalyst and volatiles removed in-vacuo. Residue is then subjected to low pressure column chromatography with 7:3 hexane:ethyl acetate as eluent. Composition and purity of isolated white solid as determined by $^1$H and $^{13}$C NMR is consistent with the brominated compound shown. (Removal of 4-[(tetrahydro-2H-pyran-2-yl)oxy] phenol by-product, if necessary, is achieved via selective acid hydrolysis in a pH 5 buffer solution, extraction into chloroform, and solvent removal. The brominated compound is stable under these conditions.)

The trans compound is obtained.

EXAMPLE IVa

4-[(tetrahydrofuran-2-yl)oxy]phenol is prepared according to the following procedure:

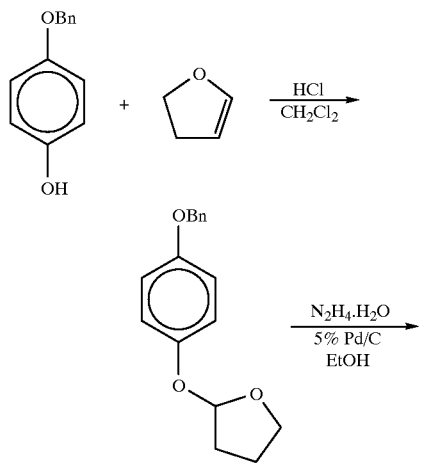

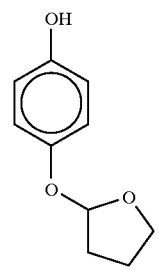

This compound is prepared according to the method of copending U.S. patent application Ser. No. 08/357,849, incorporated herein by reference.

Using an analogous method to example IV but substituting the appropriate acyclic vinyl ether, the following compounds are prepared;

| Ex | Z | (X)m | R' | R" | R''' |
|---|---|---|---|---|---|
| IVb | O | (X)o | CH$_3$ | H | Ethyl |
| IVc | O | (X)o | CH$_3$ | H | CH$_2$CH$_2$OCH$_3$ |
| IVd | O | (X)o | CH$_3$ | H | CH$_2$CH$_2$Cl |

EXAMPLE V

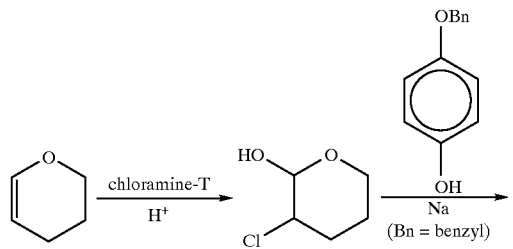

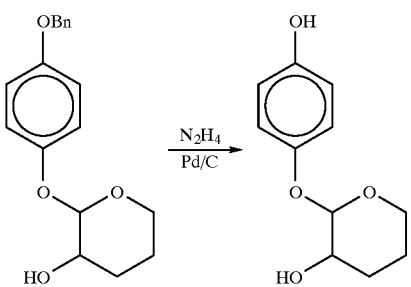

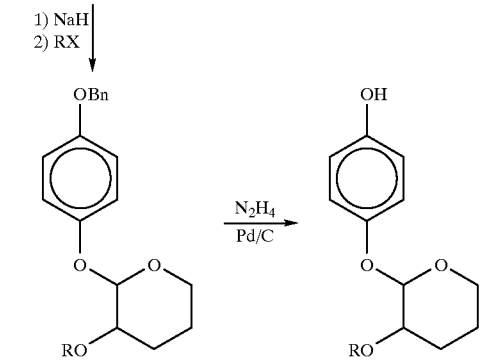

Step 1 Tetrahydro-3-chloro-2H-pyran-2-ol

Concentrated sulfuric acid (73.5 g, 0.75 mol) is added dropwise to a mixture of 3,4-dihydro-2H-pyran (63 g, 0.75 mol) and chloramine T hydrate (171 g, 0.75 mol) in 600 mL of acetone-water (1:1) while keeping the temperature under 53° C. After 1 h of stirring at room temperature, the mixture is stirred for 10 min with Et$_2$O (300 mL). The aqueous layer is separated and washed with Et$_2$O (2×200 mL). The ether layers are combined and washed with H$_2$O (2×300 mL), dried (Na$_2$SO$_4$), filtered and concentrated in vacuo. The solid residue is diluted with Et$_2$O (300 mL) and hexanes (100 mL). The suspension is stirred overnight. The mixture is filtered, and the residue (chloramine T by-product) is washed with Et$_2$O (100 mL). The filtrate and ether washing are concentrated in vacuo to an oil (103 g) which is distilled in portions via the Kugelrohr apparatus at 85–90°/0.5 mm to afford the product.

Step 2 Tetrahydro-2-[4-(benzyloxy)phenoxy]-(±)-trans-2H-pyran-3-ol

Portions of sodium metal (5.45 g, 0.237 mol) are cautiously added under argon to a solution of 4-(benzyloxy)phenol (47.5 g, 0.237 mol) dissolved in absolute EtOH (350 mL). After the sodium is consumed, a solution of chlorohydrin, (16.1 g, 0.118 mol) in absolute EtOH (90 mL) is added dropwise at room temperature. The reaction solution is stirred for 4 h then refluxed for 1 h. The cooled mixture is filtered from a trace of insoluble material (NaCl). The filtrate is evaporated in vacuo to a brown oil. The oil is partitioned between Et$_2$O-H$_2$O (600 mL-400 mL). The water layer is extracted with Et$_2$O (300 mL). The combined ether layers are dried (Na2SO4), filtered and evaporated to a white residue which is dried in vacuo to give 24.4 g of crude product. The material is dissolved in hot EtOAc (100 mL) followed by addition of hexanes (60 mL). The white solid is collected (17.2 g, impure by silica gel TLC using CH$_2$Cl$_2$-MeOH, 24:1). The solid is again dissolved in hot EtOAc (70 mL) followed by dropwise addition of hexane (15 mL). After cooling overnight the crystals are filtered to afford the product.

Step 3 4-[(3-transhydroxy-2H-pyran-2yl)oxy]phenol

Hydrazine hydrate (6.6 mL) is added to a mixture of the benzyl intermediate (11.6 g, 38.6 mmol), 10% Pd/C (0.22 g) and absolute EtOH (750 mL). The mixture is heated under argon at reflux for 1 h by which time the silica gel TLC (CH$_2$Cl-MeOH, 24:1) showed complete reaction. The mixture is cooled and filtered. The filtrate is evaporated in vacuo to a colorless solid (9.3 g) which is partitioned between EtOAc (300 mL) and H$_2$O (200 mL), dried (Na2SO$_4$), and filtered. The filtrate is evaporated to about 50 mL, heated and allowed to cool. The resultant crystals are collected, stirred with hexanes (100 mL), and then dried in vacuo at 50–55° C. to afford the product.

Compounds are prepared by the method described above, where R'O represents the term R" in the claims. For each compound made, (X)m has m=0, but compounds with m>0 are also made by this method. The following table summarizes the compounds prepared substantially as above;

| Example | RO (R") | (X)m | (CR'R')n |
|---|---|---|---|
| Va | OH (trans) | (X)o | CH$_2$CH$_2$CH$_2$ |
| Vb | OCH$_3$ | (X)o | CH$_2$CH$_2$CH$_2$ |
| Vc | CH$_3$COO | (X)o | CH$_2$CH$_2$CH$_2$ |
| Vd | OH | (X)o | CH$_2$CH$_2$ |

-continued

| Example | RO (R") | (X)m | (CR'R')n |
|---|---|---|---|
| Ve | OCH$_3$ | (X)o | CH$_2$CH$_2$ |
| Vf | CH$_3$COO | (X)o | CH$_2$CH$_2$ |

The structures of these compounds are shown below;

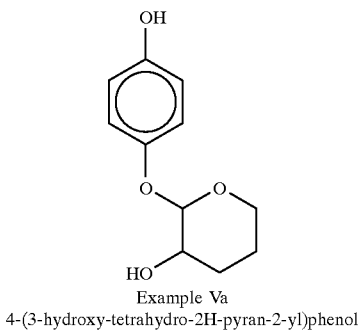

Example Va
4-(3-hydroxy-tetrahydro-2H-pyran-2-yl)phenol

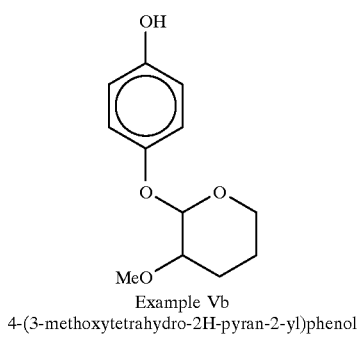

Example Vb
4-(3-methoxytetrahydro-2H-pyran-2-yl)phenol

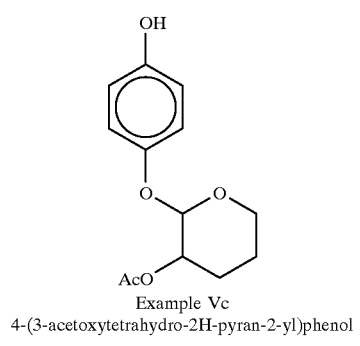

Example Vc
4-(3-acetoxytetrahydro-2H-pyran-2-yl)phenol

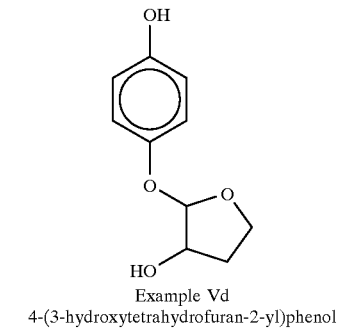

Example Vd
4-(3-hydroxytetrahydrofuran-2-yl)phenol

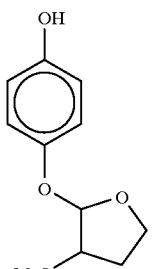

Example Ve
4-(3-methoxytetrahydrofuran-2-yl)phenol

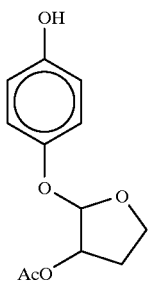

Example Vf
4-(3-acetoxytetrahydrofuran-2-yl)phenol

Examples shown above are contemplated to be quite acid resistant.

EXAMPLE VI

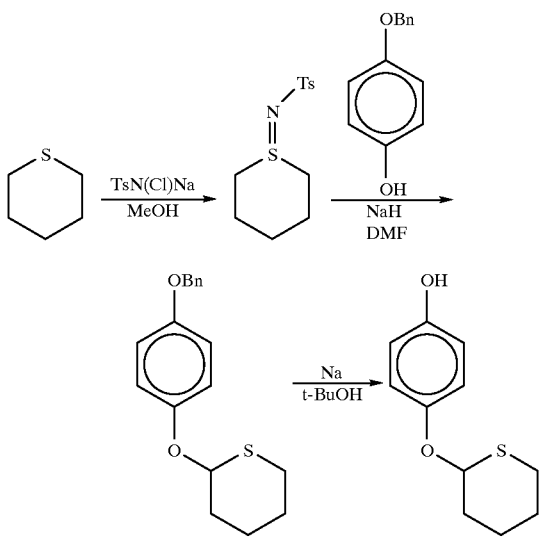

To a stirred solution of pentamethylenesulfide (25.0 g, 0.25 mol) in 450 mL of methanol is added a solution of chloramine-T (61.4 g, 0.27 mol) in 450 mL of methanol. The combined solutions are then heated at 50° C. for 4 hours, cooled and concentrated in-vacuo. The residue is washed with 400 mL of sodium hydroxide and the resulting white solid washed with water and dried in vacuo to constant weight.

In the second step, a solution of sulfilimine (21.7 g, 0.08 mol) and 4(benzyloxy)phenol (16.0 g, 0.08 mol) in 200 mL of dimethylformamide is added to sodium hydride (19.2 g, 0.48 mol) in 240 mL of dimethylformamide and stirred at room temperature for 12 hours under an inert atmosphere. Excess sodium hydride is quenched with 700 mL of ice water and the resulting milky solution extracted with diethyl ether. The organic fraction is dried over sodium sulfate, concentrated in-vacuo and the residue subjected to flash chromatography with 4:1 hexane:ethyl acetate as eluent. Composition and purity of white solid as determined by $^1$H and $^{13}$C NMR is consistent with the coupled product shown.

In step three, benzyl protected intermediate (21.2 g, 0.71 mol) is dissolved in 1.3 L of t-butanol, heated to reflux and sodium metal (12.6 g, 0.55 mol) slowly added over two hours. Further portions of sodium metal are added (10.7 g, 0.47 mol) until TLC analysis indicates most of the starting material is consumed, whereupon 150 mL of methanol is added. The solution is concentrated in vacuo and the residue partitioned between ethyl acetate (600 mL) and acetic acid (400 mL of 20%). The aqueous layer is back extracted with ethyl acetate and the organic fractions combined and dried over sodium sulfate. The resulting filtrate is concentrated in vacuo to a brown oil and purified via flash chromatography and recrystallization from hot ethyl acetate and hexane. Composition and purity of isolated 4-[(tetrahydro-2H-thiopyran-2-yl)oxy]phenol is determined by $^1$H and $^{13}$C NMR. The compound prepared by this method is 4-[(tetrahydro-2H-thiopyran-2-yl)oxy]phenol.

The compound of Example VI is optionally oxidized to sulfone or sulfoxide by treatment with peroxides, PCC or KMnO$_4$.

EXAMPLE VII

4-[(tetrahydro-2H-pyran-2-yl)oxy]phenol is prepared as follows:

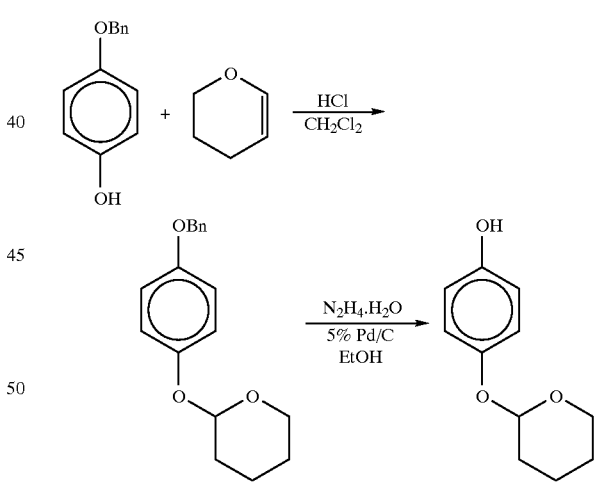

This compound is prepared as described in copending U.S. patent application Ser. No. 08/357,849, incorporated herein by reference. Composition and purity are determined by $^1$H and $^{13}$C NMR analysis.

EXAMPLE VIII

The following compounds are are prepared by the methods substantially as described in the preceeding examples. It is recognized that judicious choice of reaction conditions and starting materials is necessary and within the scope of the practice of the skilled artisan.

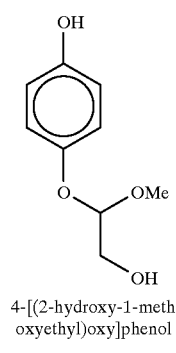
4-[(2-hydroxy-1-methoxyethyl)oxy]phenol
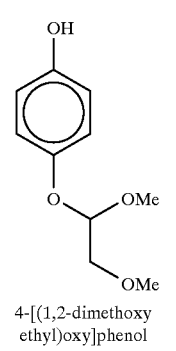
4-[(1,2-dimethoxyethyl)oxy]phenol
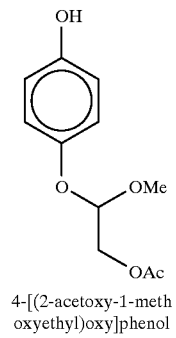
4-[(2-acetoxy-1-methoxyethyl)oxy]phenol
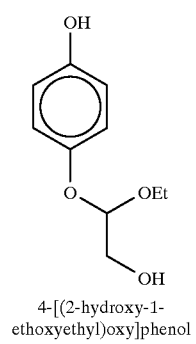
4-[(2-hydroxy-1-ethoxyethyl)oxy]phenol
Example VIIIa
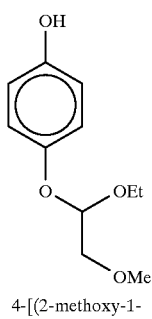
4-[(2-methoxy-1-ethoxyethyl)oxy]phenol
Example VIIIb
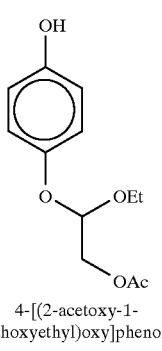
4-[(2-acetoxy-1-ethoxyethyl)oxy]phenol
Example VIIIc
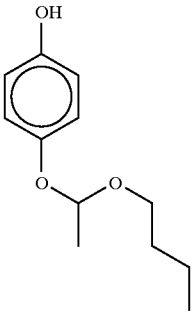
4-[(1-butoxyethyl)oxy]phenol
Example VIIId
Example VIIIe
Example VIIIf
Example VIIIg
Example VIIIh
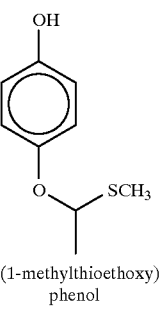
4(1-methylthioethoxy)phenol -continued

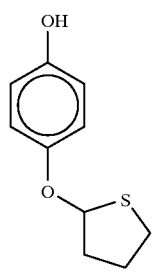

4-[(Tetrahydrothiofuran-
2-yl)oxy]phenol

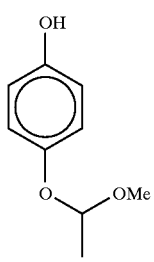

4-[(1-methoxyethyl)
oxy]phenol

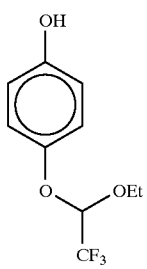

4-[(1-ethoxy-2,2,2-
trifluoro)ethoxy]phenol

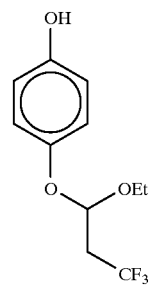

4-[(2-trifluoromethyl-1-
ethoxyethyl)oxy]phenol

-continued

Example VIIIi

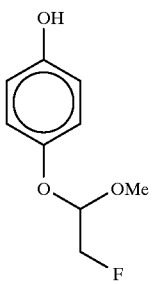

4-[(2-fluoro-1-meth
oxyethyl)oxy]phenol

Example VIIIj

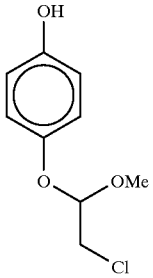

4-[(2-chloro-1-meth
oxyethyl)oxy]phenol

Example VIIIk

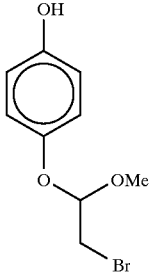

4-[(2-bromo-1-meth
oxyethyl)oxy]phenol

Example VIIIl

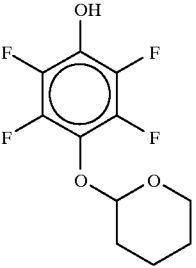

4-[(tetrahydro-2H-
pyran-2-yl)oxy]2,3,5,6-
tetrafluorophenol

Example VIIIm

Example VIIIn

Example VIIIo

Example VIIIr

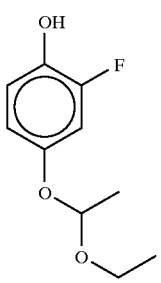

4-[(1-ethoxyethyl)oxy] 2-fluorophenol

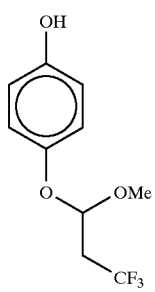

4-[(2-trifluoromethyl-1-methoxyethyl)oxy]phenol

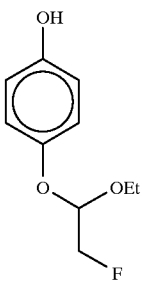

4-[(2-fluoro-1-ethoxyethyl)oxy]phenol

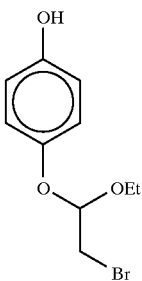

4-[(2-bromo-1-ethoxyethyl)oxy]phenol

Example VIIIt

Example VIIIu

Example VIIIv

Example VIIIw

Example VIIIx

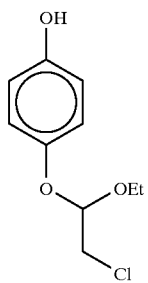

4-[(2-chloro-1-ethoxyethyl)oxy]phenol

Formulation of compositions of the invention Carriers

In addition to the active agent as described hereinbefore, the pharmaceutical compositions of this invention essentially comprise a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical compositions are capable of being commingled with the compound of the present invention, and with each other, in a manner such that there is no interaction which would substantially reduce the efficacy of the composition under ordinary use situations. Pharmaceutically-acceptable carriers must, of course, be of sufficiently high purity and sufficiently low toxicity to render them suitable for administration to the mammal being treated.

In addition, the carrier may also impart improved properties both to the composition and to the active, for example, increased bioavailability (such as by increasing or hastening penetration of topical compositions and the like) and sustained efficacy (by the stabilization of the active against hydrolysis or other attack which may occur during shelf life or use and the like), and other similar synergystic benefits. Thus it is recognized that certain actives may optionally be stabilized in formulation as well as by their design. Examples of such formulations include buffered compositions, (such as that described in copending U.S. patent application Ser. No. 08/334,466), emulsions, encapsulation (and microencapsulation, such as described in "Microcapsules-Innovative, Versatile Product Delivery: *Batelle Technical Inputs to Planning* Report #33 Columbus, Ohio (1983)) nonaqueous compositions, anhydrous compositions and the like.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; beta-cyclodextrin (β-cyclodextrin); powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; sugar; alginic acid; pyrogen-free water; isotonic saline; buffer solutions; cocoa butter (suppository base); emulsifiers, such as the Tweens®; as well as other non-toxic compatible substances used in pharmaceutical formulations. Wetting agents and lubricants such as sodium lauryl sulfate, as well as coloring agents, flavoring agents, excipients, tableting agents, stabilizers, antioxidants, and preservatives, can also be present.

The choice of a pharmaceutically-acceptable carrier to be used in conjunction with the compounds of the present invention is basically determined by the way the compound is to be administered. The preferred modes of administering the compounds of the present invention are by injection, orally and topically. The most preferred mode is topical administration. If the compound is to be injected, the injectable carrier depends upon the solubility and stability of the particular compound. Suitable pharmaceutically-acceptable carriers for topical application include those suited for use in creams, gels, tapes and the like; and for oral administration include those suited for tablets and capsules.

The pharmaceutically-acceptable carrier employed in conjunction with the compounds of the present invention is used at a concentration sufficient to provide a practical size to dosage relationship. The pharmaceutically-acceptable carriers, in total, may comprise from about 0.1% to about 99.999% by weight of the pharmaceutical compositions of the present invention, preferably from about 80% to about 99.9%, more preferably from about 90% to about 99.0%, even more preferably from about 95% to about 98.0%, also preferably about 97%.

Pharmaceutically-acceptable carriers suitable for the preparation of unit dosage forms for oral administration and injection, and dosage forms for topical application are well-known in the art. Their selection will depend on considerations like taste, cost, and/or shelf stability, and/or cosmetic look or aesthetics, feel to touch or "skin feel" etc., which are not critical for the purposes of this invention, and can be made without difficulty by a person skilled in the art. Pharmaceutically-acceptable carriers useful in the compositions of this invention are described more fully hereinafter.

A. Oral Dose Forms

Various oral dosage forms can be used, including such solid forms as tablets, capsules, granules, bulk powders and microcapsules of the drug. These oral forms comprise a safe and effective amount of a compound of this invention. Tablets can be compressed, enteric-coated, sugar-coated or film-coated containing suitable binders, lubricants, surfactants, diluents, disintegrating agents, coloring agents, flavoring agents, preservatives, flow-inducing agents, and melting agents. Liquid oral dosage forms include aqueous and nonaqueous solutions, emulsions, suspensions, solutions and/or suspensions reconstituted from non-effervescent granules, containing suitable solvents, preservatives, emulsifying agents, suspending agents, diluents, sweeteners, melting agents, coloring agents, and flavoring agents. Preferred carriers for oral administration include gelatin and propylene glycol. Specific examples of pharmaceutically-acceptable carriers and excipients that may be used in formulating oral dosage forms containing compounds of this invention are described in U.S. Pat. No. 3,903,297, Robert, issued Sep. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979), incorporated herein by reference. Techniques and compositions for making tablets (compressed, formulas and molded), capsules (hard and soft gelatin) and pills are described in *Remington's Pharmaceutical Sciences* (Arthur Osol, editor), 1553–1593 (1980), incorporated herein by reference.

The preferred unit dosage form for oral administration is tablets, capsules, elixirs and the like, comprising a safe and effective amount of a compound of this invention. Preferably oral dose forms comprise from about 10 mg to about 3500 mg of a compound of this invention, more preferably from about 25 mg to about 1000 mg, and most preferably from about 50 mg to about 600 mg.

B. Injectable Dose Forms

The compounds of this invention are also useful when injected. The dosage of the compound of this invention which is both safe and effective will vary with the particular condition being treated, the severity of the condition, the duration of treatment, the specific compound employed and its usage concentration, and like factors within the specific knowledge and expertise of the attending physician and commensurate with a reasonable benefit/risk ratio associated with the use of any drug compound. The injectable dosages and dosage ranges given herein are based on delivery of the compound of this invention to a 70 kg human and can be adjusted to provide equivalent dosages for patients of different body weights.

Methods and materials for manufacturing injectables can be found in *Remington's Pharmaceutical Sciences,* 17ed., 1985, Chapter 85, p. 1518, the disclosures of which are incorporated herein by reference in their entirety. The injectable dosage forms typically contain from about 0.001 mg/ml to about 100 mg/ml, preferably from about 0.01 mg/ml to about 10 mg/ml, more preferably from about 0.1 mg/ml to about 3.0 mg/ml, of the compound of this invention.

C. Topical Dose Forms

The compositions of this invention can also be administered topically to a ;biological subject, i.e., by the direct laying on or spreading of the composition on skin.

The topical compositions useful in this invention involve compositions suitable for topical application to mammalian skin, the composition comprising a safe and effective amount of an active agent for treatment or mixture of such actives as described hereinabove, and a pharmaceutically-acceptable topical carrier.

The topical compositions useful in this invention may be made into a wide variety of product types. These include, but are not limited to lotions, creams, beach oils, gels, sticks, sprays, ointments, pastes, essences, mousses and cosmetics. These product types may comprise several types of carrier systems including, but not limited to solutions, emulsions, gels dermal patches and solids.

The topical compositions useful in this invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dispersed or dissolved therein the skin lightening agent, and possesses acceptable safety properties (e.g., irritation and sensitization characteristics). Water is a preferred solvent. Examples of suitable organic solvents include: propylene glycol, polyethylene glycol (200–600), polypropylene glycol (425–2025), poly vinyl pyrrolidine, propylene glycol-14 butyl ether, glycerol, 1,2,4-butanetriol, sorbitol esters, 1,2, 6-hexanetriol, ethanol, isopropanol, butanediol, and mixtures thereof These solutions useful in this invention preferably contain from about 0.001% to about 10%, more preferably from about 0.01% to about 8% more preferably still from about 0.1% to about 5%, also preferably from about 0.5% to about 3% of the skin lightening agent, and preferably from about 50% to about 99.99%, more preferably from about 90% to about 99% of an acceptable aqueous or organic solvent.

If the topical compositions useful in this invention are formulated as an aerosol and applied to the skin as a spray-on, a propellant is added to a solution composition. Examples of propellants useful herein include, but are not limited to, the chlorinated, fluorinated and chlorofluorinated lower molecular weight hydrocarbons. A more complete disclosure of propellants useful herein can be found in Sagarin, *Cosmetics Science and Technology*, 2nd Edition, Vol. 2, pp. 443–465 (1972).

Topical compositions useful in this invention may be formulated as a solution comprising an emollient. An example of a composition formulated in this way would be a beach oil product. Such compositions preferably contain from about about 2% to about 50% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology* 2nd Edition, Vol. 1, pp. 32–43 (1972), incorporated herein by reference, contains numerous examples of suitable materials.

A lotion can be made from a solution carrier system. Lotions typically comprise from about 1% to about 20%, preferably from about 5% to about 10%, of an emollient; and from about 50% to about 90%, preferably from about 60% to about 80%, water.

Another type of product that may be formulated from a solution carrier system is a cream. A cream typically comprises from about 0.01% to about 20%, preferably from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). As such, these formulations provide for a system with low water content for molecules which may hydrolyze over time. Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Segarin, *Cosmetics, Science and Technology*, 2nd Edition, Vol. 1, pp. 72–73 (1972).

If the carrier is formulated as an emulsion, preferably from about 1% to about 10%, more preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al, U.S. Pat. No. 4,421,769, issued Dec. 20, 1983, Dixon et al.; and McCutcheon's *Detergents and Emulsifiers,* North American Edition, pages 317–324 (1986); the disclosures of which are incorporated herein by reference. Preferred emulsifiers are anionic or nonionic, although the other types may also be used.

Lotions and creams can be formulated as emulsions as well as solutions. Typically such lotions comprise from about 1% to about 20%, preferably from about 5% to about 10%, of an emollient; from about 25% to about 75%, preferably from about 45% to about 95%, water, and from about 0.1% to about 10%, preferably from about 0.5% to about 5%, of an emulsifier. Such creams would typically comprise from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are well known in the cosmetic art and are useful in this invention. Such emulsions can stabilize and enhance the penetration of actives. Multiphase emulsion compositions, such as the water-in-oil-in-water type, as disclosed in U.S. Pat. No. 4,254,105, Fakuda et al., issued Mar. 3, 1981, incorporated herein by reference, are also useful in this invention. In general, such single or multiphase emulsions contain water, emollients and emulsifiers as essential ingredients. Triple emulsion carrier systems comprising an oil-in-water in-silicone fluid emulsion composition as disclosed in U.S. Pat. No. 4,960,764, Figueroa, issued Oct. 2, 1990, are also useful in this invention. Judicious choice of surfactant for promotion of stability and penetration will enhance the beneficial properties of the invention.

Another emulsion carrier system useful in the topical compositions is a micro-emulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water.

Liposomal formulations are also useful compositions of this invention. These formulations can stabilize actives and also improve delivery of actives which do not penetrate well. Such compositions can be prepared by first combining a skin lightening agent with a phospholipid, such as dipalmitoylphosphatidyl choline, cholesterol and water according to the method described in Mezei & Gulasekharam, "Liposomes—A Selective Drug Delivery System for the Topical Route of Administration: Gel Dosage Form", *Journal of Pharmaceutics and Pharmacology,* Vol. 34 (1982), pp. 473–474, incorporated herein by reference, or a modification thereof. Epidermal lipids of suitable composition for forming liposomes may be substituted for the phospholipid. The liposome preparation is then incorporated into one of the above topical carrier systems (for example, a gel or an oil-in-water emulsion) in order to produce the liposomal formulation. Other compositions and pharnaceutical uses of topically applied liposomes are described in Mezei, M., "Liposomes as a Skin Drug Delivery System", *Topics in Pharmaceutical Sciences* (D. D. Breimer and P. Speiser, eds.), Elsevier Science Publishers B. V., New York, N.Y., 1985, pp. 345–358, incorporated herein by reference.

If the topical compositions useful in this invention are formulated as a gel or a cosmetic stick, such compositions can be formulated by the addition of a suitable amount of a thickening agent, as disclosed supra, to a cream or lotion formulation.

Topical compositions useful in this invention may also be formulated as makeup products, such as foundations. Foundations are solution or lotion-based with appropriate amounts of thickeners, pigments and fragrance.

The topical compositions useful in this invention may contain, in addition to the aforementioned components, a wide variety of additional oil-soluble materials and/or water-soluble materials conventionally used in topical compositions, at their art-established levels.

Various water-soluble materials may also be present in the compositions useful in this invention. These include humectants, proteins and polypeptides, preservatives, preferably buffering agents (as that described in copending U.S. patent application Ser. No. 08/334,466 incorporated herein by reference) and an alkaline agent. In addition, the topical compositions useful herein can contain conventional cosmetic adjuvants, such as dyes, opacifiers (e.g., titanium dioxide), pigments and perfumes.

The topical compositions useful in this invention may also include a safe and effective amount of a penetration enhancing agent. A preferred amount of penetration enhancing agent is from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and 4,954,487, Cooper, Loomans & Wickett, issued Sep. 4, 1990. Additional penetration enhancers useful in this invention are disclosed in Cooper, E. R., "Effect of Decylmethylsulfoxide on Skin Penetration", *Solution Behavior of Surfactants,* Vol. 2 (Mittal and Fendler, eds.), Plenum Publishing Corp., 1982, pp. 1505–1516; Mahjour, M., B. Mauser, Z. Rashidbaigi & M. B. Fawzi, "Effect of Egg Yolk Lecithins and Commercial Soybean Lecithins on In Vitro Skin Permeation of Drugs", *Journal of Controlled Release,* Vol. 14 (1990), pp. 243–252; Wong, O., J. Huntington, R. Konishi, J. H. Rytting & T. Higuchi, "Unsaturated Cyclic Ureas as New Nontoxic Biodegradable Transdermal Penetration Enhancers I: Synthesis", *Journal of Pharmaceutical Sciences,* Vol. 77, No.11 (Nov. 1988), pp. 967–971; Williams, A. C. & B. W. Barry, "Terpenes and the Lipid-Protein-Partitioning Theory of Skin Penetration Enhancement", *Pharmaceutical Research* Vol. 8, No. 1 (1991), pp. 17–24; and Wong, O., J. Huntington, T. Nishihata & J. H. Rytting, "New Alkyl N,N-Dialkyl-Substituted Amino Acetates as Transdermal Penetration Enhancers", *Pharmaceutical Research,* Vol. 6, No. 4 (1989), pp. 286–295. The above references are incorporated herein by reference. Other conventional skin care product additives may also be included in the compositions useful in this invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions useful in this invention. For example, Vitamin A, and derivatives thereof, Vitamin B2, biotin, pantothenic, Vitamin D, and mixtures thereof may be used.

Cleaning Compositions

Skin cleaning compositions useful in this invention comprise, in addition to the skin lightening agent, a cosmetically-acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the active agent in a manner such that there is no interaction which would substantially reduce the efficacy of the composition for skin lightening.

The skin cleaning compositions useful in this invention preferably contain from about 1% to about 90%, more preferably from about 5% to about 10%, of a cosmetically-acceptable surfactant. The physical form of the skin cleansing compositions is not critical. The compositions can be, for example, formulated as toilet bars, liquids, pastes, or mousses. Toilet bars are most preferred since this is the form of cleansing agent most commonly used to wash the skin.

The surfactant component of the compositions useful in this invention are selected from anionic, nonionic, zwitterionic, amphoteric and ampholytic surfactants, as well as mixtures of these surfactants. Such surfactants are well-known to those skilled in the detergency art. In addition, certain of these surfactant types may be beneficial in enhancing penetration of the active.

The cleaning compositions useful in this invention can optionally contain, at their art-established levels, materials which are conventionally used in skin cleansing compositions.

Combination Actives

A. Sunscreens and Sunblocks

Regulation of skin darkening resulting from exposure to ultraviolet light can be achieved by using combinations of the active skin lightening agents together with sunscreens or sunblocks. Useful sunblocks include, for example, zinc oxide and titanium dioxide.

Ultraviolet light is a predominant cause of skin darkening. Thus, for purposes of skin lightening, the combination of a skin lightening agent with a UVA and/or UVB sunscreen is desirable.

A wide variety of conventional sunscreening agents are suitable for use in combination with the skin lightening agent. Segarin, et al., at Chapter VIII, pages 189 et seq., of *Cosmetics Science and Technology,* disclose numerous suitable agents. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (menthyl and benzyl esters, α-phenyl cinnamonitrile; butyl cinnamoyl pyruvate); dihydroxycinnamic acid derivatives (umbelliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether; benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; 4,4'-t-butylmethoxydibenzoylmethane; and etocrylene.

Of these, 2-ethylhexyl-p-methoxycinnamate, 4,4'-t-butylmethoxydibenzoylmethane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in this invention are 2-ethylhexyl-p-methoxycinnamate, 4,4'-t-butylmethoxydibenzoylmethane, 2-hydroxy4-methoxybenzophenone, octyldimethyl-p-aminobenzoic acid and mixtures thereof Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl) methylaminobenzoic acid ester with 4-hydroxydibenzoylmethane; 4-N,N-(2-ethylhexyl) methylaminobenzoic acid ester of 2-hydroxy-4-(2-hydroxyethoxy)benzophenone; 4-N,N-(2-ethylhexyl)-methylaminobenzoic acid ester of 4-(2-hydroxyethoxy) dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof A safe and effective amount of sunscreen may be used in the compositions useful in this invention. The sunscreening agent must be compatible with the skin lightening agent. The composition preferably comprises from about 1% to about 20%, more preferably from about 2% to about 10%, of a sunscreening agent. Exact amounts will vary depending upon the sunscreen chosen and the desired Sun Protection Factor (SPF).

An agent may also be added to any of the compositions useful in this invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred skin lightening composition useful in this invention, an anti-inflammatory agent is included as an active along with the skin lightening agent. The inclusion of an anti-inflammatory agent enhances the skin lightening benefits of the compositions. The anti-inflammatory agent protects strongly in the UVA radiation range (though it also provides some UVB protection as well). The topical use of anti-inflammatory agents reduces darkening of the skin resulting from chronic exposure to UV radiation. (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions useful in this invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology* 1, R. A. Scherrer, et al., Academic Press, N.Y. (1974).

Specific non-steroidal anti-inflammatory agents useful in the composition invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and
6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the compositions are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(−)-3'-methyl-5'-hexynoyl)-2,6-di-t-butylphenol; 4-((R)-(+)-3'-methyl-5'-hexynoyl)-2,6-di-i-butylphenol; and 4-(3',3'-dimethoxypropionyl)-2,6-di-t-butylphenol are useful in methods of this invention; 4-(5'-hexynoyl)-2,6-d-t-butylphenol is most preferred.

Yet another class of anti-inflammatory agents which are useful in the compositions are those disclosed in U.S. Pat. No. 4,912,248, Mueller, issued Mar. 27, 1990. This patent discloses compounds and diastereomeric mixtures of specific 2-naphthyl- containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen- (R)-2-butyl ester, and diasteromeric mixtures of (S)-naproxol(R)-2-methyl butyrate and (S)-naproxol-(S)-2-methyl butyrate are useful in this invention.

Finally, so-called "natural" anti-inflammatory agents are useful in methods of this invention. For example, candelilla wax, alpha bisabolol, aloe vera, Manjistha (extracted from plants in the genus Rubia, particularly *Rubia Cordifolia*), and Guggal (extracted from plants in the genus *Commiphora*, particularly *Commiphora Mukul*), may be used.

Another preferred composition useful in this invention comprises a skin lightening agent, a sunscreen, and an anti-inflammatory agent together for skin lightening in the amounts disclosed for each individually hereinabove.

C. Anti-Oxidants/Radical Scavengers

In a preferred skin lightening composition useful in this invention, an anti-oxidant/radical scavenger is included as an active along with the skin lightening agent. The inclusion of an anti-oxidant/radical scavenger increases the skin lightening benefits of the composition.

A safe and effective amount of an anti-oxidant/radical scavenger may be added to the compositions useful in this invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used.

In a preferred composition useful in this invention, compositions comprise one, any two, or all three of a sunscreening agent, anti-inflammatory agent, and/or an anti-oxidant/radical scavenging agent included as actives along with the skin lightening agent. The inclusion of two or all three of these agents with the skin lightening agent increases the skin lightening benefits of the composition.

D. Chelators

In a preferred composition useful in this invention, a chelating agent is included as an active along with the skin lightening agent. As used herein, "chelating agent" means an active agent capable of removing a metal ion from a system by forming a complex so that the metal ion cannot readily participate in or catalyze chemical reactions. The inclusion of a chelating agent increases the skin lightening benefits of the composition.

A safe and effective amount of a chelating agent may be added to the compositions useful in this invention, preferably from about 0.1% to about 10%, more preferably from about 1% to about 5%, of the composition. Chelators useful in compositions are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of this invention are furildioxime and derivatives thereof.

In a preferred composition useful in this invention, compositions comprise one, any two, any three, or all four of a sunscreening agent, anti-inflammatory agent, anti-oxidant/radical scavenging agent, and/or chelating agent included as actives along with the skin lightening agent. The inclusion of two, three, or all four of these agents with the skin lightening agent increases the skin lightening benefits of the composition.

E. Retinoids

In a preferred composition useful in this invention, a retinoid, preferably retinoic acid, is included as an active along with the skin lightening agent. The inclusion of a retinoid increases the skin lightening benefits of the composition. A safe and effective amount of a retinoid may be added to the compositions useful in this invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereo isomers of these compounds, such as all-trans retinoic acid and 13-cis-retinoic acid.

In a preferred composition useful in this invention, compositions comprise one, any two, any three, any four, and/or all five of a sunscreening agent, anti-inflammatory agent, anti-oxidant/radical scavenging agent, chelating agent, and/or a retinoid included as actives along with the skin lightening agent. The inclusion of two, three, four, or all five of these agents with the skin lightening agent increases the skin lightening benefits of the composition.

Methods for Lightening Skin in Mammals

This invention relates to methods for skin lightening in mammals. Such methods comprise the administration of a safe and effective amount of a skin lightening agent to the skin or regions of the skin to be lightened. The amount of active agent and frequency of application will vary widely depending upon the pigmentation already in existence, the rate of further darkening of the skin or region of the skin, and the level of lightening desired. In addition, when the product is used to treat hyperpigmented spots, it is expected that the application and amount will differ from the amount for lightening of general skin tone.

Any dose which is less than the toxic level may be used, thus it is contemplated that for certain dosage forms, particularly topical dosage forms, the "dose" is any amount that provides the desired effect, and that amount may be so large due to frequency of application and amount applied that the maximum effective amount is irrelevant.

A safe and effective amount of skin lightening agent in a topical composition is applied, generally from about 1 µg to about 1000 mg per cm² skin per application, preferably from about 2 µg to about 800 µg/cm² skin per application, more preferably from about 30 µg to about 700 µg/cm² skin, most preferably from about 75 µg to about 250 µg/cm² skin. Application preferably ranges from about four times a day to about twice a week, more preferably from about three times a day to about once every other day, more preferably still from about once daily to about twice daily, most preferably twice daily. Application for at least five days is required to see a skin lightening effect in lower animals. After lightening is achieved, the frequency and dosage can be reduced to a maintenance level, as desired. Such maintenance varies according to the individual, but is preferably from about 1/10 to about 1/2, more preferably from about 1/5 to about 1/3 of the original dosage and/or frequency, as needed.

A preferred method of this invention for skin lightening in mammals involves applying both a safe and effective amount of the skin lightening agent and a safe and effective amount of one or more of a sunscreening agent, an anti-inflammatory agent, an anti-oxidant/radical scavenging agent, a chelating agent and/or a retinoid to the skin simultaneously. As used herein, "simultaneous application" or "simultaneously" means applying the agents to the skin at the same sites on the body at about the same time. Though this can be accomplished by applying the agents separately to the skin, preferably a composition comprising all the desired agents commingled is applied to the skin. The amount of sunscreening agent applied is preferably from about 0.01 mg to about 0.1 mg per cm² skin. The amount of anti-inflammatory agent applied is preferably from about 0.005 mg to about 0.5 mg, more preferably from about 0.01 mg to about 0.1 mg per cm² skin. The amount of anti-oxidant/radical scavenging agent preferably applied is from about 0.01 mg to about 1.0 mg, more preferably from about 0.05 mg to about 0.5 mg per cm² skin. The amount of chelating agent preferably applied is from about 0.001 mg to about 1.0 mg, more preferably from about 0.01 mg to about 0.5 mg, still more preferably from about 0.05 mg to about 0.1 mg per cm² skin. The amount of retinoid applied is preferably from about 0.001 mg to about 0.5 mg per cm² skin, more preferably from about 0.005 mg to about 0.1 mg per cm² skin. The amount of skin lightening agent applied is preferably from about 0.001 mg to about 2 mg per cm² skin per application, more preferably from about 0.01 mg to about 1 mg per cm² skin per application.

The preferred modes of administration are orally, topically, and parenterally (for example, by subcutaneous injection, intramuscular injection, intra-articular injection, intravenous injection and the like). Thus, specific modes of administration include, without limitation, oral, transdermal, mucosal, sublingual, intramuscular, intravenous, intraperitoneal, and subcutaneous administration, as well as topical application. The most preferred method of application is topical.

Oral administration can be used through oral dosing of a pharmaceutical composition comprised of a safe and effective amount of the compound of this invention in a suitable oral pharmaceutical carrier. The compound is absorbed by the gastrointestinal tract. The pharmaceutical composition may consist of solid dosage forms such as tablets, hard gelatin capsules, soft gelatin capsules, bulk powders, and microcapsules of the drug. Alternately, it may consist of a liquid dosage form such as an aqueous or nonaqueous solution, emulsion, or suspension.

The amount of the compound ingested depends upon the bioavailability of the compound from the oral pharmaceutical composition. Typically, however, the compounds of this invention are dosed in an amount of from about 0.1 mg/kg of body weight to about 500 mg/kg, and preferably from about 1 to about 100 mg/kg of body weight. The amount of the pharmaceutical composition depends upon the percent of compound within its formula, which is a function of the amount of the compound required per dose, its stability, release characteristics and other pharmaceutical parameters. Generally, the oral pharmaceutical composition should comprise from about 5% to about 50% of the compound of this invention.

The preferred method of injectable administration depends upon the solubility and stability of the particular active being used.

FORMULATION EXAMPLES

The following examples further describe and demonstrate embodiments within the scope of this invention. The examples are given solely for the purpose of illustration and are not to be construed as limitations of this invention, as many variations thereof are possible without departing from the spirit and scope of the invention.

ORAL DOSE FORMS

EXAMPLE IX

A composition for oral administration is prepared by combining the following ingredients:

| | |
|---|---|
| 4-[(3-trans-hydroxy-2H-pyran-2-yl)oxy]phenol | 1.10 kg |
| Sesame oil | 6.50 liters |

The 4-[(3-trans-hydroxy-2H-pyran-2-yl)oxy]phenol is dissolved in the sesame oil with the aid of sonication and is packaged in soft gelatin capsules using methods known in the art. Two of the resulting capsules, each containing 50 mg of the active, are administered to a 60 kg human in need of treatment.

EXAMPLE X

A composition for oral administration is prepared by combining the following ingredients:

| | |
|---|---|
| 4-[(3-cis-hydroxy-2H-pyran-2-yl)oxy]phenol | 250 g |
| Propylene glycol | 1800 ml |
| Ethyl alcohol | 175 ml |
| Distilled water | 75 ml |
| Artificial Cherry flavor | 10 ml |
| FD&C Red #40 | 0.2 g |

The above ingredients are combined to produce a syrup and are packaged under sterile conditions in 6 oz. bottles. One teaspoon of this formulation is administered to a 70 kg adult human.

EXAMPLE XI

Tablets are prepared by conventional methods, such as mixing and direct compaction, formulated as follows:

| Ingredient | mg per tablet |
| --- | --- |
| 4-[(3-trans-methoxy-2H-pyran-2-yl)oxy]phenol | 100 |
| Microcrystalline cellulose | 100 |
| Sodium Starch glycolate | 30 |
| Magnesium stearates | 5 |

One tablet is administered orally to a patient in need of treatment two times daily.

INJECTABLE DOSE FORM

EXAMPLE XII

An injectable composition is prepared as follows by combining the ingredients using conventional mixing techniques:

| Component | Weight % |
| --- | --- |
| 2-fluoro-4-[(tetrahydro-2H-pyran-2-yl)oxy]phenol | 1.0% |
| Propylene glycol:ethanol:water, 60:20:20: (w:w:w) | 94.5% |
| Dextrose | 4.50% |

A patient in need of treatment is injected once daily with 25 mls of the composition of concentration 0.4 mg/ml.

TOPICAL DOSE FORMS

EXAMPLE XIII

A simple topical composition is prepared by combining the following components utilizing conventional mixing techniques.

| Component | Percent by Weight of Composition |
| --- | --- |
| Ethanol | 85% |
| 4-[(tetrahydrofuran-2-yl)oxy]phenol | 0.05% |

This composition is applied twice daily in an amount sufficient to deposit about 0.5 μg/cm² skin for six months.

EXAMPLE XIV

A cream is prepared by combining the following components using conventional mixing techniques:

| Component | Percent by Weight of Composition |
| --- | --- |
| Water Phase | |
| U.S. Pharmacopia grade H₂O | 63.03 |
| Disodium EDTA | 0.13 |
| Glycerin | 3.00 |
| Methyl paraben | 0.25 |
| Oil Phase | |
| propylene glycol dicaprylate/dicaprate | 3.00 |
| glyceryl stearate | 4.00 |
| cetyl alcohol | 1.00 |
| stearyl alcohol | 1.00 |
| ethoxylated cetyl stearyl alcohol | 1.5 |
| Propyl paraben | 0.1 |
| Preservative Phase | |
| U.S. Pharmacopia grade H₂O | 1.49 |
| Butylene glycol | 1.50 |
| Benzyl alcohol | 0.5 |
| Active Solution | |
| 2-fluoro-4-[(tetrahydro-2H-pyran-2-yl)oxy]phenol | 3% |
| Water | 17% |

The first three phases are mixed with the active solution. The composition is applied once every other day for two months.

Preferred compounds are tested using this formulation in the pigmented guinea pig to determine their in vivo efficacy in a composition. On each guinea pig from two to six treatment sites (typically 16 cm² each) are treated topically with compounds formulated in the vehicle (100 μL of 0.1–3% active, 5× per week for up to 6 weeks) with appropriate placebo and untreated control patches on the same animal. The animals are visually and instrumentally graded for erythema and skin lightening. It is determined that the preferred compounds lightened skin without pigmentation rebound or appreciable irritation.

Based on these results, in application to a human face (approx 300 cm²), for example, about 1–2 g (or 1–2 ml) of cream is used.

EXAMPLE XV

A nonionic oil-in-water emulsion is prepared by combining the following components using conventional mixing techniques:

| Component | Percent by Weight of Composition |
| --- | --- |
| Deionized water | 78.83 |
| Propylene glycol | 3.00 |
| Octyl methoxycinnamate | 7.50 |
| Cetyl alcohol | 2.50 |
| Stearyl alcohol | 2.50 |
| Laureth 23 | 2.00 |
| C₁₂–C₁₅ Alcohols benzoate | 2.00 |
| EDTA | 0.37 |
| Methyl paraben | 0.20 |
| Propyl paraben | 0.10 |
| 4-[(tetrahydro-2H-thiopyran-2-yl)oxy]phenol | 1.00 |

The composition is applied once a day for four months. Use of an amount sufficient to deposit about 15 μg of the active per cm² skin is appropriate.

EXAMPLE XVI

A sunscreen composition is prepared by combining the following components utilizing conventional mixing techniques:

| Component | Percent by Weight of Composition |
| --- | --- |
| Polypropylene glycol 15 Stearyl ether | 15.00 |

-continued

| Component | Percent by Weight of Composition |
| --- | --- |
| Sorbitan oleate | 2.00 |
| Octyl methoxy cinnamate | 7.50 |
| Propyl paraben | 0.15 |
| Butylated hydroxy toluene | 0.05 |
| Cyclomethicone | 20.00 |
| Sesame Oil | 5.00 |
| Mineral Oil (Blandol) | 50.30 |
| 4-[(1-ethoxyethyl)oxy]phenol | 7.00 |

The above composition is applied twice a week for five months. Use of an amount sufficient to deposit 100 μg of the active per cm² skin is appropriate.

EXAMPLE XVII

| Component | Percent by Weight of Composition |
| --- | --- |
| Deionized Water | 89.63 |
| EDTA | 0.37 |
| 2-fluoro-4-[(tetrahydro-2H-pyran-2-yl)oxy]phenol | 10.00 |

The above composition is applied once every three days for three months. Use of an amount sufficient to deposit 120 μg of the active per cm² skin is appropriate to lighten hyperpigmented regions.

While particular embodiments of this invention have been described, it will be obvious to those skilled in the art that various changes and modifications of this invention can be made without departing from the spirit and scope of the invention. It is intended to cover, in the appended claims, all such modifications that are within the scope of the invention.

What is claimed is:

1. A method for lightening mammalian skin comprising orally administering to a mammal in need of such treatment a safe and effective amount of a composition comprising:

a) an effective amount of a skin lightening active having the structure;

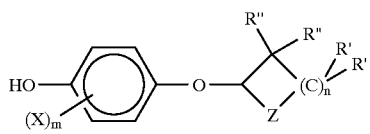

wherein:
   (i) each X is, independently, selected from the group consisting of halo, $C_1$–$C_{10}$ alkyl, substituted $C_1$–$C_{10}$ alkyl, substituted or unsubstituted phenyl, substituted or unsubstituted naphthyl, OR, OCOR, COR, CONRR, COOR, CN, SR, SOR, $SO_2R$, $SO_3R$ and NRR; wherein X is other than hydroxy, amino or thio if this X is attached ortho to the phenol hydroxy;
   (ii) m is an integer from 0 to 4;
   (iii) each R' and each R" is independently selected from the group consisting of hydrogen, halo, $C_1$–$C_{10}$ alkyl, substituted $C_1$–$C_{10}$ alkyl, substituted or unsubstituted phenyl, substituted or unsubstituted naphthyl, OR, OCOR, OCRROR, COR, CR(OR)OR, CONRR, COOR, CRROR, CN, SR, and NRR; wherein halo, when it appears, is other than germinal to a hydroxy, $NH_2$ or SH;
   (iv) each R is, independently, selected from the group consisting of hydrogen, $C_1$–$C_{10}$ alkyl, substituted $C_1$–$C_{10}$ alkyl, substituted or unsubstituted phenyl, and substituted or unsubstituted naphthyl;
   (v) n is an integer from 1 to 5, wherein (C)n adjacent to Z has other than amino, SH, CN or hydroxy as R';
   (vi) Z is selected from the group consisting of O, NR, S, $SO_2$, $RO_2R$ and POR; and
   (vii) wherein any carbon, when disubstituted, having as one substituent selected from the group consisting of hydroxy, amino, cyano and thiol, has the other substituent selected from the group consisting of hydrogen, alkyl, substituted or unsubstituted phenyl, and substituted or unsubstituted naphthyl, whether this substituent is R' or R"; and b) a pharmaceutically-acceptable carrier therefor.

2. A method for lightening mammalian skin comprising injecting a mammal in need of such treatment, with a safe and effective amount of the composition used in the method according to claim 1, at least once or more monthly.

3. A method for lightening mammalian skin comprising topically applying to the skin of a mammal in need of such treatment, a safe and effective amount of the composition used in the method according to claim 1, so as to deliver from about 30 μg to about 750 μg of the compound per cm² skin, at least once or more monthly.

4. A method for lightening mammalian skin comprising, topically applying to the skin of a mammal in need of such treatment, a safe and effective amount of the composition used in the method according to claim 1 in which the skin lightening active has a Jmax of at least about 2 μg/cm²/h, so as to deliver from about 30 μg to about 750 μg of the compound per cm² skin, at least once or more monthly.

5. A method for lightening mammalian skin comprising topically applying to the skin of a mammal in need of such treatment, a safe and effective amount of the composition used in the method according to claim 1, in which the skin lightening active is selected from the group consisting of 4-[(tetrahydro-2H-pyran-2-yl)oxy]phenol, 4-[(tetrahydro-2H-thipyran-2-yl)oxy]phenol, 2-fluoro-4-[(tetrahydro-2H-pyran-2-yl)oxy]phenol, and 4-[(tetrahydrofuran-2-yl)oxy]phenol, so as to deliver from about 30 μg to about 750 μg of the compound per cm² skin, at least once or more monthly.

6. The method of claim 3, wherein lightening mammalian skin comprises lightening hyperpigmented regions of skin.

7. A method for lightening mammalian skin comprising orally administering to a mammal in need of such treatment, a safe and effective amount of a composition comprising a) an effective amount of a skin lightening active having the structure:

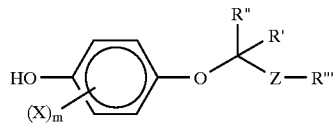

wherein:
   (i) each X is, independently, selected from the group consisting of halo, $C_1$–$C_{10}$ alkyl, substituted $C_1$–$C_{10}$ alkyl, substituted or unsubstituted phenyl, substituted or unsubstituted naphthyl, OR, OCOR, COR, CONRR, COOR, CN, SR, SOR, $SO_2R$, $SO_3R$ and NRR; wherein X is other than hydroxy, amino or thio if this X is attached ortho to the phenol hydroxy;
   (ii) m is an integer from 0 to 4;
   (iii) R' and R" are independently selected from the group consisting of hydrogen, $C_1$–$C_{10}$ alkyl, substituted $C_1$–$C_{10}$ alkyl, substituted or unsubstituted phenyl, substituted or unsubstituted naphthyl, COR, CR(OR)OR, CONRR, COOR, and CRROR, wherein when R' is hydrogen, R" is other than hydrogen;

(iv) R''' is $C_1$–$C_{10}$ alkyl or substituted $C_1$–$C_{10}$ alkyl;

(v) each R is, independently, selected from the group consisting of hydrogen, $C_1$–$C_{10}$ alkyl, substituted $C_1$–$C_{10}$ alkyl, substituted or unsubstituted phenyl, and substituted or unsubstituted naphthyl; and (vi) Z is selected from the group consisting of O, NR, S, SO, $SO_2$, $PO_2R$ and POR; and b) a pharmaceutically-acceptable carrier therefor.

8. A method for lightening mammalian skin comprising injecting a mammal in need of such treatment, with a safe and effective amount of the composition used in the method according to claim 7, at least once or more monthly.

9. A method for lightening mammalian skin comprising topically applying to the skin of a mammalian in need of such treatment, a safe and effective amount of the composition used in the method according to claim 7, so as to deliver from about 30 µg to about 750 µg of the compound per $cm^2$ skin, at least once or more monthly.

10. The method of claim 9, wherein lightening mammalian skin comprises lightening hyperpigmented regions of skin.

* * * * *